US008037880B2

(12) United States Patent
Zhu et al.

(10) Patent No.: US 8,037,880 B2
(45) Date of Patent: Oct. 18, 2011

(54) DRY POWDER INHALER

(75) Inventors: Jingxu Zhu, London (CA); Jianzhang Wen, London (CA); Yingliang Ma, London (CA); Hui Zhang, London (CA)

(73) Assignee: The University of Western Ontario, London, Ontario (CA)

( * ) Notice: Subject to any disclaimer, the term of this patent is extended or adjusted under 35 U.S.C. 154(b) by 936 days.

(21) Appl. No.: 11/399,616

(22) Filed: Apr. 7, 2006

(65) Prior Publication Data

US 2007/0235029 A1 Oct. 11, 2007

(51) Int. Cl.
*A61M 15/00* (2006.01)

(52) U.S. Cl. .............................. 128/203.12; 128/203.15

(58) Field of Classification Search ............. 128/203.12, 128/203.14, 200.14, 200.16, 200.23, 200.24, 128/203.15, 203.21, 203.19; 206/528; 222/144
See application file for complete search history.

(56) References Cited

U.S. PATENT DOCUMENTS

| | | | | |
|---|---|---|---|---|
| 4,627,432 | A * | 12/1986 | Newell et al. | 128/203.15 |
| 5,323,936 | A * | 6/1994 | Wolter et al. | 222/401 |
| 5,388,572 | A * | 2/1995 | Mulhauser et al. | 128/203.15 |
| 5,577,497 | A * | 11/1996 | Mecikalski et al. | 128/203.15 |
| 5,642,727 | A * | 7/1997 | Datta et al. | 128/203.15 |
| 5,921,237 | A | 7/1999 | Eisele | |
| 5,975,076 | A | 11/1999 | Yianneskis | |
| 6,006,747 | A | 12/1999 | Eisele | |
| 6,055,980 | A | 5/2000 | Mecikalski | |
| 6,089,228 | A | 7/2000 | Smith | |
| 6,116,239 | A | 9/2000 | Volgyesi | |
| 6,209,538 | B1 | 4/2001 | Casper | |
| 6,257,732 | B1 | 7/2001 | Takahagi | |
| 6,325,061 | B1 | 12/2001 | Dagsland | |

(Continued)

FOREIGN PATENT DOCUMENTS

CA 21777032 6/1995

(Continued)

OTHER PUBLICATIONS

Dunbar et al.,"Dispersion and Characterization of Pharmaceutical Dry Powder Aerosols", KONA, No. 16, 1998, pp. 7-45.

(Continued)

*Primary Examiner* — Justine Yu
*Assistant Examiner* — Valerie L Skorupa
(74) *Attorney, Agent, or Firm* — Lynn C. Schumacher; Hill & Schumacher

(57) ABSTRACT

A new dry powder inhaler is developed as a pulmonary medicine delivery device for dispersing precise tiny dosages (10 μg-50 mg) of pure carrier-free ultra-fine powdered medicament (<5 μm aerodynamics particle size) into a patient's lung. The powder is drawn from the blister cell and dispersed through an outlet tube assisted by two air streams. The first air stream goes through a the blister cell from its upstream side, to significantly fluidize the medicament in the dose to flow upward. The second one extracts the fluidized powder from downstream of the blister cell for further deagglomeration and dispersion of the medicament powder by shear force. The rotating multi-dose blister can hold up to 60 doses, which are pre-metered with pure ultra-fine powdered medicament. So that it has higher drug loading capability in small volumes, compared to most current dry powder inhalers, which usually use some excipient. The inhaler efficiently disperse the aerosolized medicament in the air stream to the deep interior of patient's lung. The fine particle fraction (<4.7 μm) is reported to reach as high as 80% using this inhaler.

60 Claims, 19 Drawing Sheets

U.S. PATENT DOCUMENTS

| | | | | |
|---|---|---|---|---|
| 6,401,712 | B1 * | 6/2002 | von Schuckmann | 128/203.15 |
| 6,684,917 | B2 * | 2/2004 | Zhu et al. | 141/18 |
| 7,387,122 | B2 * | 6/2008 | Nishibayashi et al. | 128/203.15 |
| 2001/0029948 | A1 * | 10/2001 | Ingle et al. | 128/203.15 |
| 2002/0033176 | A1 * | 3/2002 | Casper et al. | 128/203.15 |
| 2003/0178024 | A1 * | 9/2003 | Allan et al. | 128/200.24 |
| 2005/0109659 | A1 * | 5/2005 | Hickey et al. | 206/538 |

FOREIGN PATENT DOCUMENTS

| | | |
|---|---|---|
| CA | 2187787 | 10/1995 |
| CA | 2202919 | 5/1996 |
| CA | 2227594 | 2/1997 |
| CA | 2262562 | 2/1998 |
| CA | 2284060 | 9/1998 |
| CA | 2322183 | 9/1999 |
| WO | WO 00/43059 | 7/2000 |
| WO | WO 2005002654 A2 * | 1/2005 |

OTHER PUBLICATIONS

Smith et al., “The inhalers of the future? A review of dry powder devices on the market today”, Pulmonary Pharmacology & Therapeutics, vol. 16, 2003, pp. 79-95.

Geldart, D., “Types of gas gluidization”, Powder Technology, vol. 7, 1973, pp. 285-292.

Dalby et al., “A review of the developement of Respimat® Soft Mist™ Inhaler”, Int'l J. of Pharmaceutics, vol. 283, 2004, pp. 1-9.

Spallek et al., “Scale-up and production challenges of bringing Respimat® Soft Mist™ Inhaler (SMI) to market”, Respiratory Drug Del., vol. 9, 2004, pp. 263-270.

“Guidance for Industry: Metered Dose Inhaler (MDI) and Dry Powder Inhaler (DPI) Drug Products”, US Dept. of Health and Human Services, Nov. 13, 1998, 62pages.

* cited by examiner

DRY POWDER INHALER

FIELD OF THE INVENTION

The present invention relates to a method and device delivering fine dry powders, and more particularly the present invention relates to a method and device for pulmonary drug delivery.

BACKGROUND OF THE INVENTION

Pulmonary drug delivery represents a new drug administration method that provides many advantages. It provides direct and fast topical treatments for respiratory and lung diseases. It avoids the first-pass GI (gastrointestinal) metabolism and can provide targeted delivery to heart and brain. Large molecules such as peptides and proteins can be systemically delivered using the pulmonary channel. Pulmonary drug delivery also allows the use of drugs with low solubility. Most peptide and protein drugs are far more stable in the solid rather than liquid state. Antibiotics and even vaccines can be delivered in this manner. Compared to oral in-take, it provides a fast and much more efficient adsorption. Typically, only a few percent of the medication of the oral in-take is required for pulmonary delivery due to that many drugs degrade in the digestive tract before they are absorbed. Compared to intravenous injection, it provides a painless and safer alternative.

Numerous methods can be employed to generate drug aerosols in therapeutically useful size ranges and concentrations [A. J. Hickey, Inhalation Aerosols: Physical and Biological Basis for Therapy, New York, 1996]. Specifically, these are metered-dose inhalers (MDIs), dry powder inhalers (DPIs), and nebulizers, that can achieve minimally acceptable characteristics in simple, convenient, inexpensive, and portable format.

Nebulizers such as jet nebulizers or ultrasonic nebulizers are used for the delivery of aqueous pharmaceuticals and are generally large in design and complex to operate, so that they are more for clinical use. The precision of the dose administered to the patient is highly dependent on a variety of factors such as atmospheric temperature and humidity, as well as the volume and strength of the patient's breathing. Metered Dose Inhalers (MDI) suspends or dissolves the ultra-fine drug powders into liquid propellants and stores them. When a metered quantity of the propellant is released from the storage canister, the propellant evaporates and expands quickly to disperse the powdered drug or liquid droplet drug into the patients' mouth. The propellant can be a chlorofluorocarbon, a hydrochlorofluorocarbon, or a hydrocarbon, some of which are unfavourable due to environmental concerns. The another key problem with this method is that the quick expansion of the propellant causes the drug to impact in the back of the throat, reducing the amount being inhaled into the lung to about 20-30% [Guidance for Industry: Metered Dose Inhaler (MDI) and Dry Powder Inhaler (DPI) Drug Product, U.S. Department of Health and Human Services, 1998]. More recent developments with improvement in design, such as the new SoftMist inhaler, has claimed a high FPF (fraction of fine particles), which suggests a higher lung deposition rate [M. W. Spallek, J. Geser, H. Reincke, and A. Moser, Scale-up and production challenges of bringing Respimat SoftMist inhaler (SMI) to market, *Respiratory Drug Delivery IX,* 2004, and R. Dalby, M. W. Spallek, and T. Voshaar, A review of development of Respimat SoftMist Inhaler, *Int. J. Pharmaceutics,* 2003]. In general, however, the MDI method needs good breath coordination and it is difficult to predict the amount of drug inhaled if the patients' inhalation does not coincide with the drug releasing.

Dry powder inhaler (DPI) is similar to a metered dose inhaler in that it also delivers a precisely measured dose medicine into the lungs, but in dry powder form. It is designed to generate a drug powder aerosol onto or via the inspiratory air flow. It has been proved that powder aerosols can carry approximately five times more drug in a single breath than metered dose inhaler (MDI) systems and many more times than liquid or nebulizer systems.

To facilitate pulmonary delivery, drug powders should normally be less than 5 μm (or equivalent aerodynamic diameter) so that they become airborne during inhalation. However, powders of such small sizes (typical group C powder in the Geldart classification) [D. Geldart, Types of Gas Fluidization, *Powder Technology*, Vol. 7, 285-297, 1973] have very strong inter-particle forces that make them agglomerate and very difficult to handle. The agglomeration of powder is normally formed prior to delivery due to the inter-particle forces, and possible moisture absorption. Agglomerated drug powders become difficult to dispense completely from the doses, and/or, is dispensed at least partially as larger agglomerates, thereby significantly reducing the lung deposition efficiency.

To overcome the inter-particle forces, current industrial practice applies two different methods; one is the suspension of the powder into liquid in Metered Dose Inhalers (MDIs) as described above, and the other involves mixing the ultra-fine drug powders with large amounts of coarser powder. This method uses a large quantity of excipient (filler) particles that are much larger (normally group A or group A-C powders in the Geldart classification). This makes the small-large powder mixture fluidize easily so that they can be handled easily. It also significantly increases the volume of each dosage so that the dispensing and packing becomes more accurate relatively. This is practiced for most dry powder inhaler (DPI) currently on the market. However, only a small fraction of the small drug particles can detach effectively from the large excipient particles during inhalation and the rest stay with the large particles and land in the mouth. This limits the efficiency of final delivery for DPIs to about 6-14%. [I. J. Smith, M. Parry-Billings, The Inhalers of the Future? A Review of Dry Powder devices on the Market Today, *Pulmonary Pharmacology & Therapeutics* 16, 79-95, 2003].

The current designs of dry powder inhalers (DPIs) can be divided into two types, the pre-metered and the device-metered ones [Guidance for Industry: Metered Dose Inhaler (MDI) and Dry Powder Inhaler (DPI) Drug Product, U.S. Department of Health and Human Services, 1998] both of which can be driven by patient inspiration alone (Passive dry powder inhaler) or with some power-assistance (Active dry powder inhaler) [Guidance for Industry: Metered Dose Inhaler (MDI) and Dry Powder Inhaler (DPI) Drug Product, U.S. Department of Health and Human Services, 1998] Pre-metered DPIs contain previously measured doses in single or multiple presentations in blisters, capsules, or other cavities that are subsequently inserted into the device during manufacture or by the patient before use. Thereafter, the dose may be inhaled directly from the unit or it may be transferred to a chamber before being inhaled by the patient. Device-metered DPIs have an internal reservoir containing sufficient formulation for multiple doses being metered by the device itself during actuation by the patient.

Passive dry powder inhalers rely on the aspiratory flow as the sole source of energy for powder fluidization, deagglomeration and inhalation. A number of such inhalers have been developed. These include the Ultrahaler (Aventis), the Clichhaler (Asmabec), Turbuhaler (Astra), and Diskus (GlaxoSmithKline) [I. J. Smith, M. Parry-Billings, The Inhalers of the Future? A Review of Dry Powder devices on the Market Today, *Pulmonary Pharmacology & Therapeutics* 16, 79-95, 2003 and C. A. Dunbar, A. J. Hickey and P. Holzner, Dispersion and Characterization of Pharmaceutical Dry Powder Aerosols, *KONA,* 16, 7-45, 1998].

The AstraZeneca Turbulhaler is a multiple dose inhaler with 50, 100 or 200 doses of active drug stored in a reservoir [U.S. Pat. No. 6,257,732, U.S. Pat. No. 6,325,061,1. J. Smith, M. Parry-Billings, The Inhalers of the Future? A Review of Dry Powder devices on the Market Today, *Pulmonary Pharmacology & Therapeutics* 16, 79-95, 2003 and C. A. Dunbar, A. J. Hickey and P. Holzner, Dispersion and Characterization of Pharmaceutical Dry Powder Aerosols, *KONA,* 16, 7-45, 1998]. The drug is metered into small doses by scrapers inside the inhaler. Air enters the inhaler and passes through the dosing unit, fluidizing the powder by shear force. The turbulence in the narrow inhalation channel, the impaction on the bottom of the mouthpiece, and high shear stress in the swirl nozzle of the mouthpiece help the particle deagglomateration. In this inhaler, it includes two metering and inhalation processes. It is unique in dispensing minute quantity of drug powders without the use of an added carrier.

The Diskus [I. J. Smith, M. Parry-Billings, The Inhalers of the Future? A Review of Dry Powder devices on the Market Today, *Pulmonary Pharmacology & Therapeutics* 16, 79-95, 2003 and C. A. Dunbar, A. J. Hickey and P. Holzner, Dispersion and Characterization of Pharmaceutical Dry Powder Aerosols, *KONA,* 16, 7-45, 1998] is a blister pack, unit-dose device. The pack consists of a coiled, double-foil strip of 60 blisters, each containing one dose of drug powder with a lactose carrier. The drug can be in the 50-500 μg range. During inhalation, each blister is moved into place, and its lid-foil is peeled away by a contracting wheel. The inhaled air is drawn through the opened blister, aerosolizing and delivering the dose through the mouthpiece.

Clickhaler [C. A. Dunbar, A. J. Hickey and P. Holzner, Dispersion and Characterization of Pharmaceutical Dry Powder Aerosols, *KONA,* 16, 7-45, 1998] consists of a metering cone, bulk drug reservoir, and compression spring. It holds 100 or 200 doses of drug. Only one metered dose is present in the inhalation passage at any one time. The inhaler should be held approximately upright during priming and inhalation, and a rapid and deep inhalation is needed for optimal dose delivery.

Active dry powder inhalers have an additional source of energy than that provided by inhalation to fluidize and disperse the powder. The Nektar Pulmonary Inhaler [U.S. Pat. No. 6,089,228] is a gas-assisted dry powder inhaler. It comprises a relatively large transparent holding chamber with a powder inlet at one end of the feed chamber. The powder inlet has a receptacle where a foiled dosage containing the medicament can be penetrated and a pressurization cylinder providing high pressure air stream extract the powdered medicament from the receptacle to the chamber and disperse in flowing compressed gas to form an aerosol. It is claimed that this kind of inhaler provides an efficient pulmonary delivery of accurate, precise, and repeatable dosages of powdered medicaments. A patient pulls a hand pump to compress a small charge of air, inserts a packet of drug powder into the slot, then presses the firing button to disperse the powder into an aerosol cloud The inhaler generates the aerosol independently of patient inspiratory flow rate, and it is Ideal for large and small molecules with 2-5 mg doses.

The SPIROS™ (Dura) has a breath activated, motor driven impeller which provides electromechanical energy to disperse the powder [C. A. Dunbar, A. J. Hickey and P. Holzner, Dispersion and Characterization of Pharmaceutical Dry Powder Aerosols, *KONA,* 16, 7-45, 1998]. The Prohaler™ (Valois) is a multi-dose powder inhaler where a built-in pump gives compressed air to facilitate dose metering and powder dispersion [C. A. Dunbar, A. J. Hickey and P. Holzner, Dispersion and Characterization of Pharmaceutical Dry Powder Aerosols, *KONA,* 16, 7-45, 1998].

The additional energy input decreases or eliminates the dependence of the aerosolization process on the patient's breathing ability, increases the fine particle fraction in aerosol flow and ensures effective powder dispersion [C. A. Dunbar, A. J. Hickey and P. Holzner, Dispersion and Characterization of Pharmaceutical Dry Powder Aerosols, *KONA,* 16, 7-45, 1998]. However, these kinds of inhalers can be big and heavy, are not very convenient for patient use, and also its cost can be much higher than desired. Additionally, breath coordination becomes very important for the active DPIs in most cases, as patient inhalation and aerosolization needs to be synchronized.

Currently, the most popular formulation of powder for DPIs consists of the drug that is usually blended with a carrier (lactose or glucose) to facilitate flow and dispersion. The suitability of a carrier is dependent on its chemical and physical characteristics, which can have direct effect on the performance of the product such as ease of entrainment of the formulation, energy input necessary for dispersion and aerosolization of the active ingredient from the carrier. It would be ideal if the required small quantity of the fine drug powder could be accurately dispensed alone, without any carrier/incipient. When only the pure drug powder is packaged into the inhaler, if the particle aggregates can be dispersed into primary particles (<5 μm), the delivery efficiency is expected to increase significantly. Considering that many drugs are quite expensive, typically being many times more costly than conventional drugs, it is very critical to be able to efficiently deliver the dry powders to the target region of the lung with minimal loss of the drug.

There are various types of inhalers for delivering a dry powdered medicament. For example, U.S. Pat. No. 6,116,239 discloses an inhalation device for use in delivering a powdered substance to a user. It comprises a holding portion for holding the powder substance, an air entry passageway having an inlet port open to an exterior of the device to direct air entering it and to fluidize the medicament upon inhalation by the user. A hold-up chamber is for holding the fluidized medicament and maintaining the substance in a fluidized state, then to deliver them to the user through an air exit passageway. The hold-up chamber is cylindrically shaped and has a longitudinally extending axis around which air is inhaled. The powder substance is claimed to be effectively deaggregated almost immediately upon inhalation and form a relatively uniform concentration of powder.

U.S. Pat. No. 5,975,076 discloses a dry powder inhaler which comprises a reservoir of medicament powder, a dispensing chamber for receiving a charge of powder to be dispensed, an air passage having an inlet terminating at a nozzle directed downwardly into the dispensing chamber. Air is drawn in through the inlet to enter the dispensing chamber as a jet through the nozzle in a direction which is both downwardly onto the medicament and laterally across the chamber with respect to the mouthpiece.

U.S. Pat. No. 5,921,237 describes a drug powder inhaler including a cover plate pivotally attached to a lid on the inhaler housing. A blister pack disk is rotatably mounted on the housing under the cover plate. An actuator in the housing is most desirably aligned with a lever on the cover plate.

When a patient pushes the actuator, it presses to shear open a blister on the blister pack disk and delivers the drug in the dose in the blister into a staging chamber for inhalation by the user.

In U.S. Pat. No. 6,006,747, a dry powder inhaler has a multi-dosage medicine containing cartridge attached on the top of the housing, and a cartridge ring with apertures for holding dry powder medicine. The housing includes a mixing or aerosolizing chamber. A pressure switch is located in the housing for actuating the mixing process within the chamber. A lid is pivotally attached to the housing and is used to index or advance the cartridge ring to a next aperture for delivery of successive drug dosages. During inhalation, a pressure differential develops across the venturi air passageway and reaches a predetermined level, then the motor is turned on by the pressure switch.

U.S. Pat. No. 6,055,980 describes a dry powder inhaler comprising: a housing, a mixing chamber in the housing, an impeller within the space of the mixing chamber, a motor linked to the impeller, at least one inlet opening leading into the mixing chamber, and at least one outlet opening leading out of the mixing chamber. The device uses breath-actuation and is generally independent of patient coordination. A motor spins the impeller at high speed. A plunger introduces a dose of powdered medicine into the chamber so that all powder particles are available for intermixing disaggregation and comminution. The drug-laden air flows out of the chamber and into a mouthpiece. It provides a proper mixing of air and powdered drug particles for inhalation by a patient.

U.S. Pat. No. 6,209,538 describes an inhalation-activated dry powder inhaler, that has a primary inhalation passage extending through the housing, and a secondary inhalation passage disposed in communication with the primary inhalation passage and a source of medicament. As the user's inhalation reaches a defined rate, the flow inhibiting mechanism restricts flow through the primary inhalation passage and moves the blocking plate to enable airflow through the secondary passage. The medicament is provided through the secondary inhalation passage, thereby optimizing the delivery of medicament to the lungs.

Most of these dry powder inhalers are ideal for large amount medicament delivery (with 2-5 mg per dose). The formulation of the powder used is usually blended with large particle carriers. There are several problems related to delivery of small quantity of dry powder pharmaceuticals with these inhalers. First, these inhalers all apply an air entry passageway and an air exit passageway on the same side of blister or cartridge. The powder is extracted from its receptacle only by shear force. When the drug receptacle becomes too small drug powder is too cohesive, it becomes difficult to draw entire dry powder completely out from the receptacle and break up the particle aggregates. This will reduce the efficiency of the delivery. Secondly, these devices usually achieve delivery of fine drug particles by a two-step dispersion. It uses a chamber for receiving and maintaining the fluidized drug powder then deliver them to the user. This will cause some waste of expensive drug powder and decrease the accuracy of delivery due to the fine powder stuck on the surface of the chamber. Furthermore, some of the delivery devices are large or expensive, and inconvenient for changing for different medicaments and different dosage sizes.

There is therefore a need for an inhaler that is capable of accurately delivering small precise amounts of expensive powder drugs with minimal powder handling, in a compact and inexpensive instrument which does not require the need for excipients.

SUMMARY OF THE INVENTION

The present invention addresses the need for a dry powder inhaler that can deliver small accurate volumes of powder. The present invention provides a new method and apparatus for a dry powder inhaler for accurate delivery of powdered medicaments for pulmonary drug delivery. Based on the patented technology, a volumetric metering fluidized bed such as disclosed in (U.S. Pat. No. 6,684,917 B2) can preferably used to precisely dispense a pre-determined amount of pure powdered medicaments (without any excepient) into a receiver such as a described multi-dose blister pack forming part of the dry powder inhaler. This patented device can deliver a powder plume with approximately 90% or more of the inhalable particles (less than 5 μm in diameter or equivalent aerodynamic diameter) in their primary particle form, that is, with less than 10% particle agglomerates for the small inhalable particles. This ensures the accurate and uniform dispensing of the inhalable particles into the blister cells (receptacles) of a blister pack forming part of the dry powder inhaler devices disclosed herein.

This blister pack with multiple dosages is loaded into the dry powder inhaler. With its flow-through blister cells and an optional dual air flow mechanism, powder inside the blister cells is easily extracted out and excellent dispersion of medicament powder is achieved during inhalation. In particular, there is no need for larger excipient particles which have been used in many existing inhalers to enhance the powder flow and to assist the breakup of and/or to prevent the formation of agglomerates.

The present invention is most suitable for the very precise delivery of very tiny dosages of pure powdered medicaments, giving the very high delivery efficiency. This is particularly useful for the delivery of very expensive medicaments such as peptide and protein drugs, for which the use of excipient will significantly reduce the delivery efficiency and therefore significantly increase the cost. It is also useful for the systemic delivery or localized delivery of any powdered medicament through the lungs.

The inhaler can extract and entrain substantially the entire amount of powder within the receptacle. Up to about 90% of drug emitted from a dose of the inhaler is delivered into patient's respiratory tract. Fine particle fraction of the drug (<4.7 μm) is typically from 60% to 80%, when exiting the inhaler, as measured with the Anderson cascade impactor at 28.3 L/min and the NGI (Next Generation Impactor). It has been reported that most existing dry powder inhalers can only deliver a small fraction (about 10-30%) of the dispensed drug in the correct particle sizes for lung deposition.

The present invention optionally provides a rotating multi-dose blister with dosages of pre-metered pure drug or drug with either none or a minimum amount of excipient. The blister pack is arranged to have a sufficient number of doses for a patient to use during a convenient long period. The carrier-free inhaler has the advantage of smaller dosage forms and high dosage concentration, which can provide significant savings when using expensive drugs. It is a critical technical challenge to achieve both adequate dispersion and small disperse volumes. Small dosages can also avoid choking during inhalation.

According to the method of the present invention, the pure powdered medicament is contained in a small pocket of the blister with a porous filter at its bottom. Due to shelf storage, the medicament may have partially reagglomerated and would need to be dispersed during inhalation. The medicament can be drawn out by a negative pressure resulting from the patient's suction or a positive pressure from a small pressurized gas canister located in the inhaler housing or by the user pressurizing the interior of the inhaler housing in embodiments using telescoping housing sections. Thus extraction and deaggregation of the powder medicament can be achieved by inspiration effort alone, or a combination of inhalation and positive pressure from the bottom side of the blister. The air stream, due to inhalation or pressurized gas, or both, can be divided into two flow streams. The first one pierces into the blister through a bottom plate of a blister pack and filter. It provides sufficiently high air velocity to mobilize, fluidize and deagglomerate the drug powder stored in each individual blister. The second air stream flows to the top of the blister pack through an appropriate positioned channel, and meets the powder dose at the top of the small powder pocket or blister from which the drug powder is to be dispersed. It provides an additional shear fluidization to entrain the fluidized powder in the airflow, then to carry the entrained powder into the mouthpiece of the inhaler, so that the inhaler can break up most of the agglomerates and assure efficient delivery of the powder with minimum losses.

The present invention has several major advantages. First, the entire amount of drug powder in the blister can be drawn out of the pocket completely. This is because the first stream of fluidization air flows through the small pocket from its bottom and directly blow the powder out of the pocket. This is unlike the commonly used inhalers, where only a tangential flow from the top is used to pick up the powder from the pocket. Secondly, it is easy to break up agglomerates, if any, into individual particles with two streams of airflow. These two airflow streams produce two different dispersion effects on the fine powder. It can significantly reduce the efforts for inhaling the medicine and perfectly aerosolize the ultra-fine powder. Thirdly, the high speed of the second airflow can help break up the agglomerates of particles completely. The ratio of the first airflow and the second airflow is adjustable for different drugs to improve the effect of dispersion. The inhaler eliminates the need for an aerosolized powder holding chamber and directly disperses the powdered drug into the mouthpiece of the inhaler. This reduces the amount of medicament trapped on the surface of the chamber, and further improves the drug delivery efficiency and accuracy. The inhaler also does not depend on the respiratory capacity of the patient even when it is used under negative pressure, because the amount of air required to extract and deliver the medicament is extremely low in comparison with human inhalation capacity. This is clearly an advantage for patients with respiratory diseases. In addition, the inhaler is of simple design which eliminates unnecessary complexity; the device is completely mechanically controlled and extremely compact. It is easy to use, and has very high patient reproducibility.

Therefore, in one aspect of the invention there is provided a dry powder inhaler for dispensing powder medicament, comprising:

a) a housing and mounting means for mounting a blister pack in an interior of said housing, said blister pack including a holding plate and a plurality of powder pockets substantially filled with a powder comprising a pre-selected amount of powder medicament, said powder pockets formed from a plurality of holes extending through the holding plate, said housing including a first gas flow inlet passageway and an outlet flow passageway; and b) positioning means for positioning said blister pack to bring each powder pocket into flow communication with said outlet flow passageway and said first gas flow inlet passageway, said first gas flow inlet passageway having an inlet in flow communication with a source of gas and an exit located in said housing on one side of said powder pocket, said outlet flow passageway having an inlet located in said housing on the other side of said powder pocket which is positioned in flow communication with said outlet flow passageway and an outlet on an exterior of said housing, wherein when gas from the source of gas is flowed into said first gas flow inlet passageway it flows into one side of said powder pocket and through the powder pocket to mobilize, fluidize and deagglomerate the powder medicament such that a mixture of powder medicament and gas flows out through the other side of said powder pocket and into said outlet flow passageway and out of said outlet.

The present invention also provides a method of dispensing a powder medicament contained in a plurality of powder pockets in a blister pack mounted in an inhaler, the method comprising the steps of:

a) moving the blister pack to bring a powder pocket into flow communication with an outlet flow passageway and a first gas flow inlet passageway in the inhaler, the blister pack including a holding plate and the plurality of powder pockets substantially filled with a powder comprising a pre-selected amount of powder medicament, said powder pockets formed from a plurality of holes extending through the holding plate, the first gas flow inlet passageway having an inlet in flow communication with a source of gas and an exit located on one side of the powder pocket, said outlet flow passageway having an inlet located on the other side of the powder pocket positioned in flow communication with the outlet flow passageway and an outlet on an exterior of said housing;

b) fluidizing the powder medicament contained in the powder pocket which is aligned with the first gas flow inlet passageway and the outlet passageway using a first flow of gas from the gas flow inlet passageway which flows into one side of the powder pocket and through the powder pocket to mobilize, fluidize and deagglomerate the powder medicament such that a mixture of powder medicament and gas flows out through the other side of said powder pocket and into said outlet flow passageway and out of said outlet;

c) withdrawing said fluidized powder out of said inhaler through said outlet passageway; and d) repeating steps a), b) and c) as many times as needed to dispense a needed amount of the powder medicament.

The present invention also provides a method of pulmonary drug delivery of a powder medicament into a user's respiratory system, comprising the steps of:

a) substantially filing powder pockets of a blister pack with a powder comprising a fine powder medicament selected from the group consisting of peptides or fragments thereof, proteins or fragments thereof, antibodies or fragments thereof, antibiotics, vaccines and any combination thereof, and loading the blister pack into a dry powder inhaler;

b) moving the blister pack to bring a powder pocket into flow communication with an outlet flow passageway and a first gas flow inlet passageway in the dry powder inhaler, the first gas flow inlet passageway having an inlet in flow communication with a source of gas and an exit located on one side of the powder pocket, said outlet flow passageway having an inlet located on the other side of the powder pocket positioned in flow communication with the outlet flow passageway and an outlet on an exterior of said housing;

c) fluidizing the powder medicament contained in the powder pocket which is aligned with the first gas flow inlet passageway and the outlet passageway using a first flow of gas from the gas flow inlet passageway which flows into one side of the powder pocket to mobilize, fluidize and deagglomerate the powder medicament such that a mixture of powder medicament and gas flows out through the other side of said powder pocket and into said outlet flow passageway and out of said outlet through a mouthpiece inserted in a user's mouth so that powder medicament is expelled out through the mouthpiece and directly into the user's respiratory system; and d) repeating steps b) and c) as many times as needed to dispense a needed amount of the powder medicament.

In yet another aspect of the invention, there is provided a dry powder inhaler for dispensing powder medicament, comprising:

a) a housing and mounting means for mounting a blister pack in an interior of said housing, said blister pack including a holding plate and a plurality of powder pockets containing a pre-selected amount of powder medicament formed from a plurality of holes extending through the holding plate, said housing including a first gas flow inlet passageway and an outlet flow passageway; and b) positioning means for positioning said blister pack to bring each powder pocket into flow communication with said outlet flow passageway and said first gas flow inlet passageway, said first gas flow inlet passageway having an inlet in flow communication with a source of gas and an exit located in said housing on one side of said powder pocket, said outlet flow passageway having an inlet located in said housing on the other side of said powder pocket which is positioned in flow communication with said outlet flow passageway and an outlet on an exterior of said housing; and c) a second gas flow inlet passageway having an inlet and an exit, said exit being positioned adjacent to the powder pocket which is positioned in flow communication with said outlet flow passageway;

wherein when gas from the source of gas is flowed into said first gas flow inlet passageway it flows into one side of said powder pocket and through the powder pocket to mobilize, fluidize and deagglomerate the powder medicament such that a mixture of powder medicament and gas flows out through the other side of said powder pocket and into said outlet flow passageway and out of said outlet, and wherein gas in said second gas flow inlet passageway is directed transversely over said other side of said powder pocket to further assist fluidization and entrainment of the medicament powder.

Preferably, the fine powder medicament does not contain excipient powder particles.

BRIEF DESCRIPTION OF THE DRAWINGS

The invention will now be described, by way of non-limiting examples only, reference being made to the accompanying drawings, in which.

DETAILED DESCRIPTION OF THE PREFERRED EMBODIMENTS

Figure 1A:
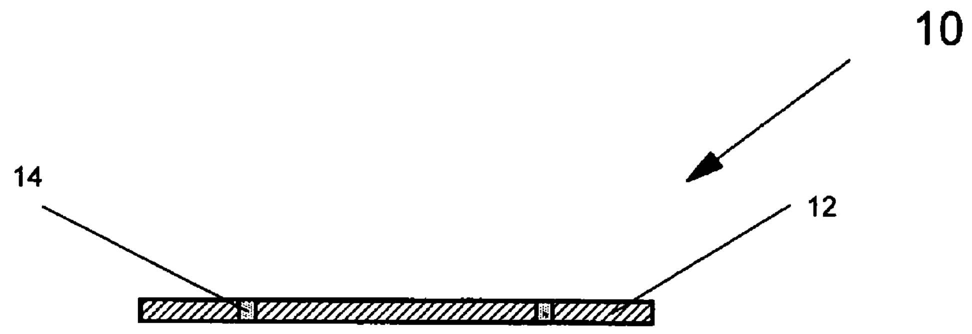
FIG. 1*a* is a side view of an embodiment of a blister pack constructed in accordance with the present invention.
Figure 1B:
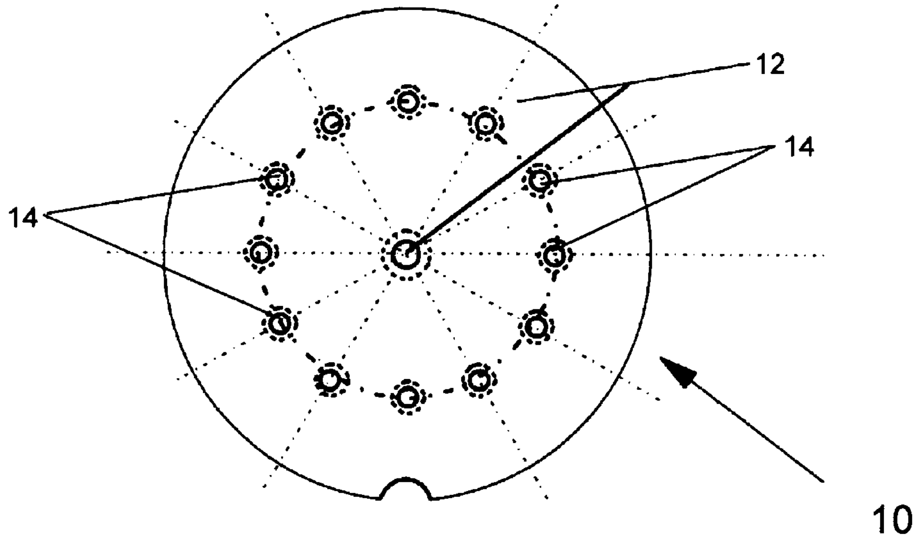
FIG. 1*b* is a top view of the embodiment of the blister pack shown in FIG. 1*a;*

In the following description, like numerals in the different embodiments refer to the same or very similar parts. FIGS. 1*a* and 1*b* show an embodiment of a blister pack 10 that is used to hold multi-doses of a powdered medicament. The blister pack 10 contains a (holding) plate 12 with multiple powder pockets 14 extending through the plate in which the medicament is contained. The powder pockets 14 formed in the holding plate 12 which contain the powder medicament are also referred to as blisters or blister cells. Powdered medicament is pre-charged into the blisters or blister cells 14 which is then put into an inhaler to be discussed hereinafter. By introducing a gas flow through the blisters 14, the charged powder medicament will be blown out, to form a powder flow for the pulmonary drug delivery, as will be described in detail hereinafter.

The blister cells 14 in the holding plate 12 are normally identical in size and have a fixed or pre-selected volume to store a pre-selected amount of powder therein. By changing the holding plates 12 with different pocket diameters and plate thickness, blister packs 10 of different volumes can be obtained. Any number of powder pockets 14 can be arranged in any fashion in the plate 12, but for easy use in the inhalers it is beneficial that powder pockets 14 are arranged along certain circles on the disk. In the illustrated blister pack of FIG. 1, the holding plate 12 is circular and the powder pockets 14 are arranged on the circumference of a circle. However, more powder pockets 14 may be arranged on multiple circles on the plate 12.

Figure 17A:
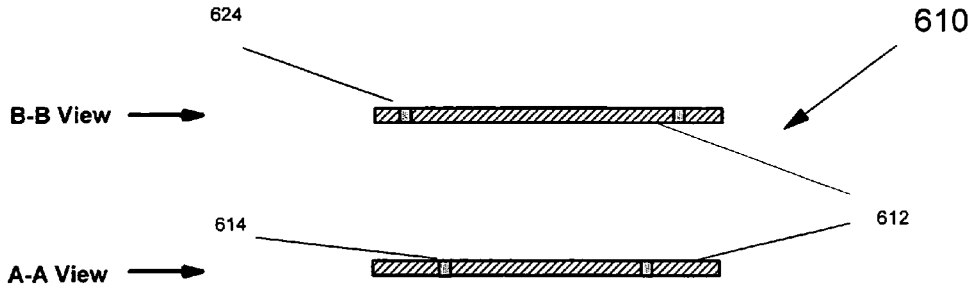
FIG. 17*a* is a side cross sectional view of an alternative embodiment of a blister pack that has a double circle arrangement of blister cells or pockets.
Figure 17B:
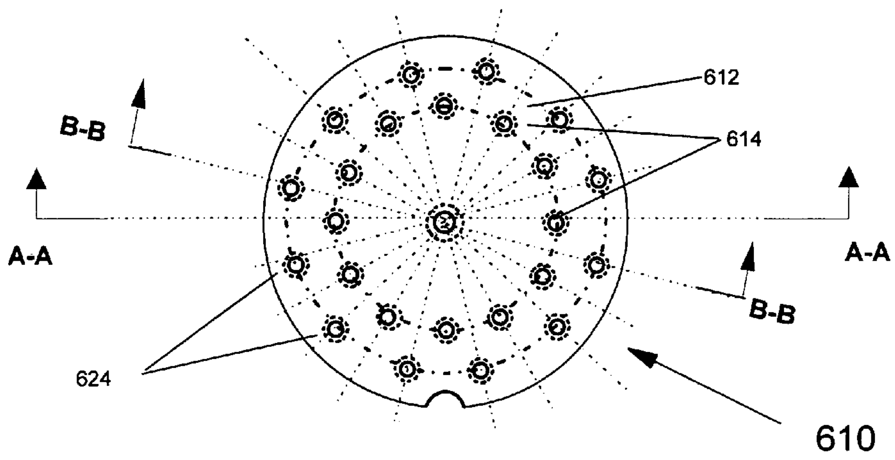
FIG. 17*b* is a top view of the blister pack of FIG. 17*a*.

FIGS. 17*a* and 17*b* shows an embodiment of an alternative blister pack 610 that has a double circle arrangement of pockets. The blister pack 610 contains a holding plate 612 with an inner circle of multiple pockets 614 and an outer circle of pockets 624 arranged in two concentric circles. As before, the powder pockets 614 and 624 in the two circles formed in the holding plate 612 which contain the powder medicament are also referred to as blisters or blister cells. Powdered medicament is pre-charged into the blisters or blister cells 614 and 624 after which the blister pack 610 is inserted into an inhaler. By introducing a gas flow through each of the blisters 614 and 624, the charged powder medicament will be blown out, to form a powder flow for the pulmonary drug delivery, as will be described in detail hereinafter. The blister cells 614 and 624 in the holding plate 612 are normally identical in size and have a fixed or pre-selected volume to store a pre-selected amount of powder therein. By changing the holding plates 612 with different pocket diameters and plate thickness, blister packs 610 of different volumes can be obtained. Any number of powder blisters 614 and 624 can be arranged in any fashion in the plate 612, but for easy use in the inhalers it is beneficial that powder blisters 614 and 624 are preferably arranged in two concentric circles on the plate 612. In the illustrated blister pack of FIG. 17, the holding plate 612 is circular and the blisters 614 and 624 are arranged on the circumferences of two concentric circles.

The blister cells 14 in plate 12 in FIGS. 1*a* and 1*b*, and blister cells 614 and 624 in plate 612 in FIG. 17*b*, may be made of any shape, although a vertical cylindrical shape is preferred since it is the easiest to produce and to align with the powder outlet channel. For example, vertically tapered holes with increasing diameter towards the top surface of plate 12 and 612 would be beneficial for the easy charging and blowing-off of the powder.

Figure 2:
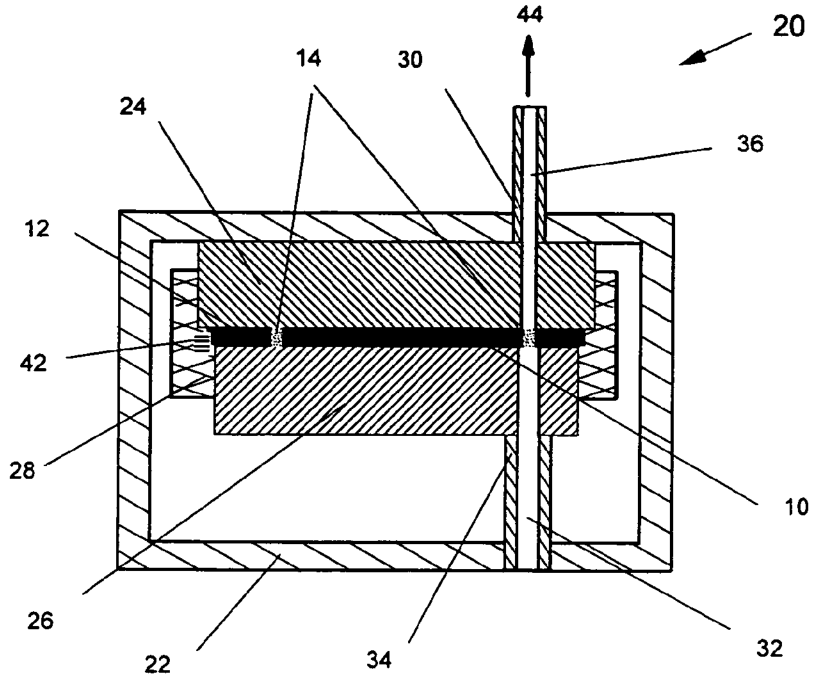
FIG. 2 is a cross sectional view of an inhaler, which depends on the patient-generated air flow and creates a small airflow from the bottom surface of the blister pack to the mouth piece at the top of the blister.
Figure 3:
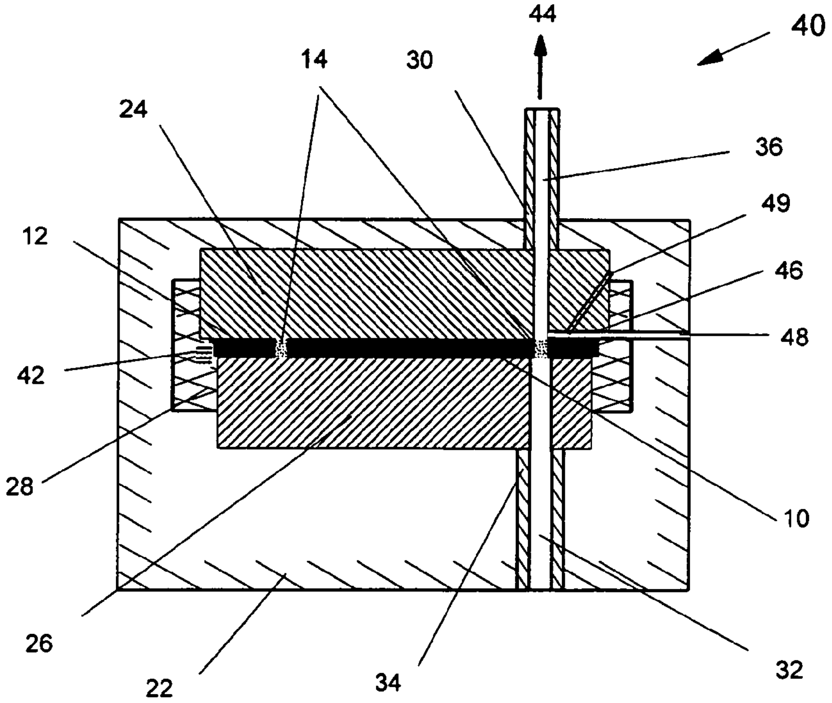
FIG. 3 is a cross sectional view of another embodiment of an inhaler, modified from the inhaler shown in FIG. 2 by having an additional stream of flow assistance air at the access port of the pocket to help the fluidization and deaggoleration of the powder from the pockets.
Figure 4:
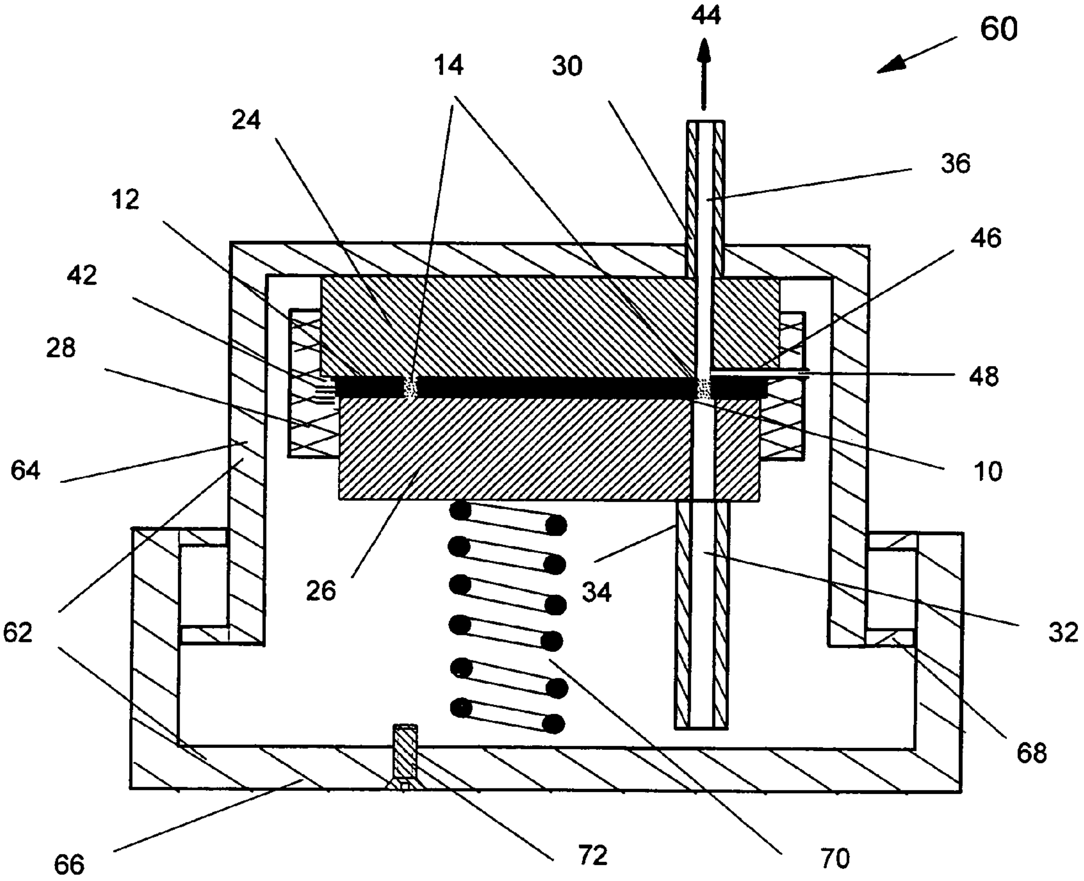
FIG. 4 is a cross sectional view of another embodiment of an inhaler similar to the inhaler shown in FIG. 3, where both airflow streams are provided by a pressurized air source that is generated by a piston at the bottom of the inhaler.

FIGS. 2 to 4 show different embodiments of inhalers constructed in accordance with the present invention. Referring first to FIG. 2, an inhaler 20 includes a cylindrical housing 22 which holds a circular disc-shaped blister pack 10 (FIG. 1) which contains several individual blister cells 14, each containing a known amount of powdered medicament, arranged in one or more circles on the blister pack 10. Housing 22 includes a gas flow inlet tube 34 which encloses a flow passageway 32 on the bottom of housing 22 and an air flow outlet tube 30 positioned above a blister cell 14 at the top of the blister pack 10 which encloses a flow passageway 36. The blister pack 10 is sandwiched between, and held in place, by a top seal block 24 and a bottom seal block 26. With a locking pin 42, the blister pack 10 is tightly fixed with a ratchet wheel 28, which can be rotated in steps to align in turn each of the individual pocket holes in the holding plate 12 with the flow passageways 32 and 36. The ratchet wheel 28 is used to rotate the blister pack 10 and to align and hold in place each blister cell 14 aligned with the passageway 32 (as well as 36) through which the powder is to be dispensed. From the top of air flow outlet tube 30, and in the direction indicated by arrow 44, a patient can suck the powder contained in the powder blister 14 adjacent to passageway 36 with a gas in passageway 32.

The gas flow inlet tube 34 which encloses the flow passageway 32 on the bottom of housing 22 may include an adjustable constriction means for adjusting gas flow in passageway 32 to allow adjustment of the gas flow rate.

Figure 18:
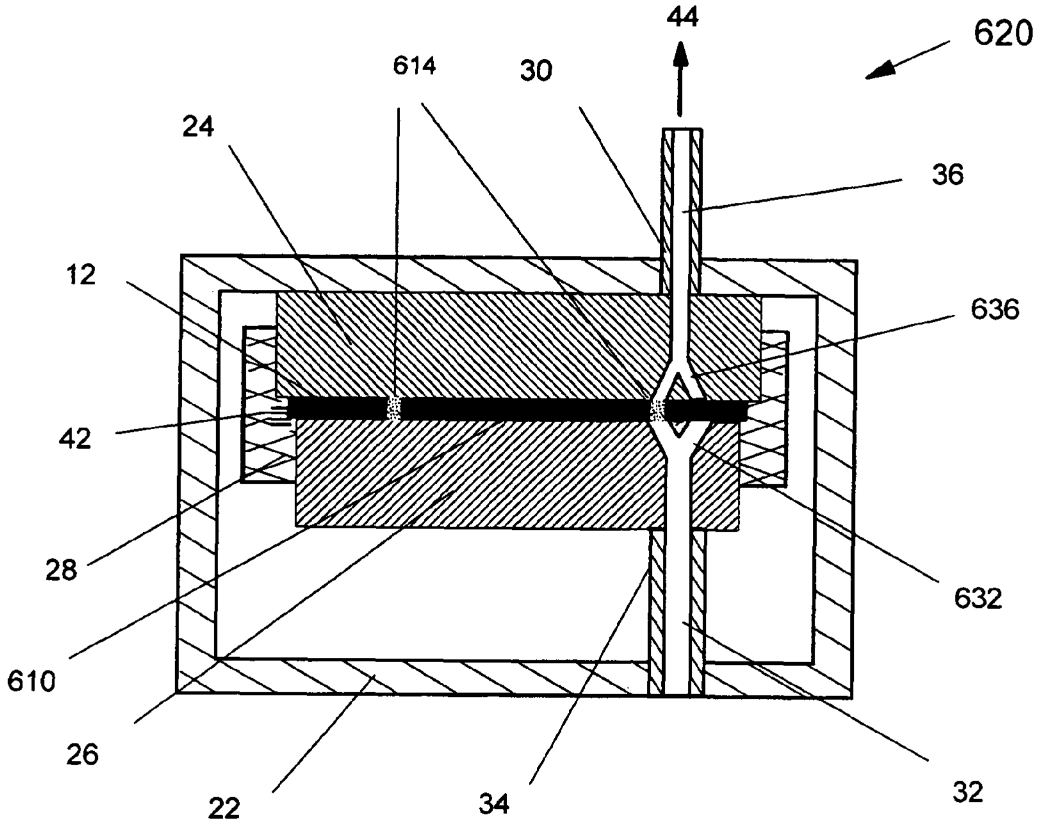
FIG. 18 is a cross sectional view of an inhaler that is designed to receive the blister pack of FIGS. 17*a* and 17*b*.

FIG. 18 shows an inhaler arrangement 620 that is designed for holding the blister pack 610 (FIGS. 17*a* and 17*b*) with two concentric circles of blister pockets. The inhaler 620 includes a cylindrical housing 22 which holds a circular disc-shaped blister pack 610 which contains several individual blisters 614 and 624 (624 is not shown on the plane sectioned in FIG. 18), each containing a known amount of powdered medicament, arranged in two circles on the blister pack 610. Housing 22 includes a gas flow inlet tube 34 which encloses a flow passageway 32 on the bottom of housing 22 and an air flow outlet tube 30 positioned above a blister cell 614 at the top of the blister pack 610 which encloses a flow passageway 36. The blister pack 610 is sandwiched between, and held in place, by a top seal block 24 and a bottom seal block 26. The top part of the bottom gas flow inlet tube 34 has a Y shaped branching 632 extending into two directions each pointing to the positions of blisters in the inner and outer circles. Likewise, the bottom part of the top air flow outlet tube 30 also has a Y shaped branching 636 extending into two directions each pointing to the positions of blisters in the inner and outer circles.

With a locking pin 42, the blister pack 610 is tightly fixed with a ratchet wheel 28, which can be rotated in steps to align in turn each of the individual pocket holes 614 and 624 in the holding plate 612 with the flow passageways 32 and 36. The ratchet wheel 28 is used to rotate the blister pack 610 and to align and hold in place alternatively each blister cell 614 aligned with left branch of Y shape 632 in the passageway 32 and each blister cell 624 aligned with right branch of Y shape 632 in the passageway 32. Likewise, the left branch of the Y shape 636 is aligned with blisters 614 and the right branch of the Y shape 636 is aligned with blisters 624, alternatively. Through the gas passageway through either the left branches or the right branches, alternatively, the powder in the blisters on the inner circle or blisters on the outer circle is to be dispensed.

For the inhalers 20 and 620 shown in FIGS. 2 and 18, the powdered medicament can be drawn out by a negative pressure resulting from the patient's suction from the top of the air flow outlet tube 30 or a positive pressure from the bottom of the gas flow inlet tube 34. The latter can be provided by connecting a small compressed gas canister with an activation means or by the in-situ compression of a telescope section as shown in FIG. 4 below.

FIG. 3 shows a cross sectional view of an alternative embodiment of an inhaler device at 40. Inhaler device 40 is very similar in structure to device 20 of FIG. 2 but includes an additional small air flow inlet tube 46, defining a flow passageway 48, located just above the holding plate 12 of the blister pack 10, which is positioned at 90 degrees to outlet tube 30 and which sweeps the top surface of the powder blister 14 adjacent to passageway 36 to entrain the powder out of the powder blister 14 aligned with outlet passageway 36. With the assistance of this additional air flow through passageway 48, the dispensing of the powder medicament is easier and more efficient than using the airflow from the inlet tube 32 alone. The relative ratio between the air flow through passageway 32 and the air flow through passageway 48 is determined by the relative flow resistance through the two passageways, mostly by the diameter and the length of the two passageways. A large diameter pipe for passageway 48 would increase the air flow rate which is used for sweeping gas across the top surface of the powder blister 14 and for entraining the powder out of the powder blister 14. To further adjust the flow ratio, a small screw 49 is set through the top block 24 and ends at the wall of the air inlet tube 46. To decrease the air flowrate through passageway 48, the small screw can be advanced into the air inlet tube 46, creating additional flow resistance inside passageway 48. It will be understood that all embodiments of the inhalers disclosed herein having the two gas flow passageways may include this adjustable screw 49 to provide gas flow constriction, or any other type of gas flow constriction mechanism may be used.

FIG. 4 is a cross sectional view of another inhaler 60 which differs from inhaler 40 in that the housing 62 is constructed of a housing in two sections, an upper section 64 and a lower section 66 which move in telescoping relationship to each other for pressurizing the air entering passageway 32 located in the chamber defined by housing sections 64 and 66. A spring 70 is located between the bottom of housing section 66 and the bottom surface of seal block 26 which acts to bias housing section 66 away from housing section 64. Housing section 64 includes a shoulder 68 around the periphery of the end portion located within housing section 66 with shoulder 68 extending outwardly to engage the inwardly protruding peripheral edge of section 66 in order to hold the two housing sections 64 and 66 together. At the bottom of housing section 66, there is a threaded hole which is normally blocked off by a screw 72. When needed, this screw 72 can be removed to allow airflow through the hole. The flow passageway 48 created by tube 46 as shown in FIG. 4 is optional and its addition can further help the entrainment of powdered medicament.

Inhaler 60 as shown in FIG. 4 provides for the production of a back pressure inside the chamber formed by housing sections 64 and 66 that can be used to disperse the powder from the blister cell aligned with passageway 36. On the other hand, when the screw 72 is removed, inhaler 60 essentially becomes inhaler 40 of FIG. 3. When the screw 72 is threaded into the hole and sealed properly, as a patient squeezes housing sections 64 and 66 together the air in the interior chamber is pressurized thereby producing a compressed air flow up through passageway 32 flowing up through the bottom of the powder blister 14 and in through the small air passageway 48 which sweeps across the top of powder blister cell 14 aligned with passageway 36. The compressed air flows up through passageway 32 and fluidizes the powder in the blister cell 14 of the blister pack 10, then entrains and disperses the powder efficiently with the assistance air flow in passageway 48.

The blister pack 10 shown in FIGS. 1*a* and 1*b* may be charged with powdered medicament using the rotating fluidized bed disclosed in U.S. Pat. No. 6,684,917 B2 or other suitable means that can dispense powder accurately into the blister cells. After dispensing powder into the blister cells 14, the charged blister pack 10 may be covered on one or both sides with protection layers such as aluminum foils or other means, to prevent the powder from falling out and/or prevent moisture from getting into the packed cell with packed powder. Before loading the blister pack 10 into the inhaler 60, the protective films are removed.

The blister pack 10 shown in FIGS. 1*a* and 1*b* is, however, only one embodiment and is likely the simplest embodiment. More complicated blister packs can be made that further ensure the accuracy of final pulmonary drug delivery.

Figure 5A:
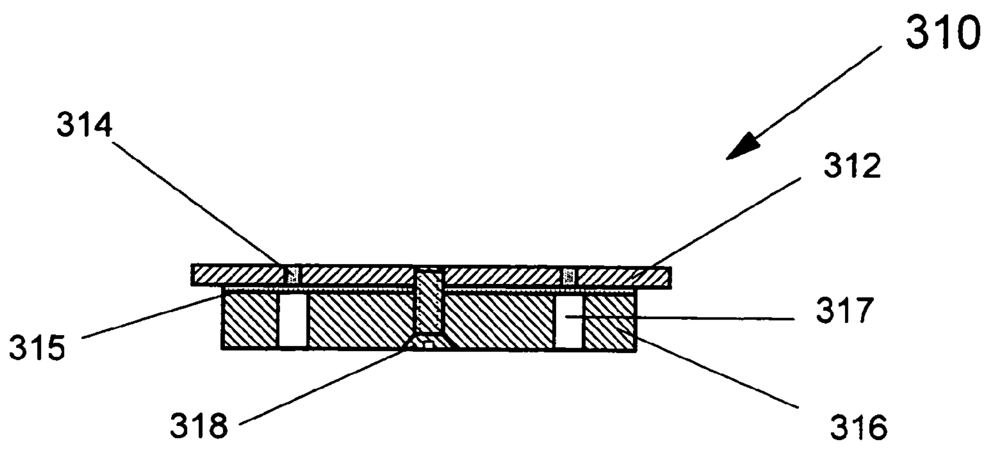
FIG. 5*a* is a cross sectional view of another embodiment of a blister pack.
Figure 5B:
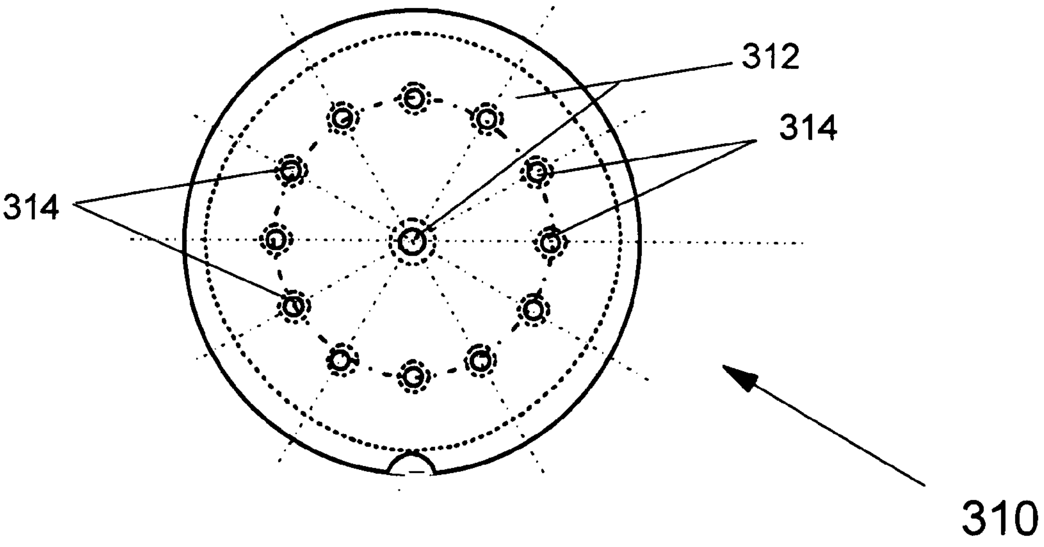
FIG. 5*b* is a top view of the blister pack of FIG. 5*a;*
Figure 6:
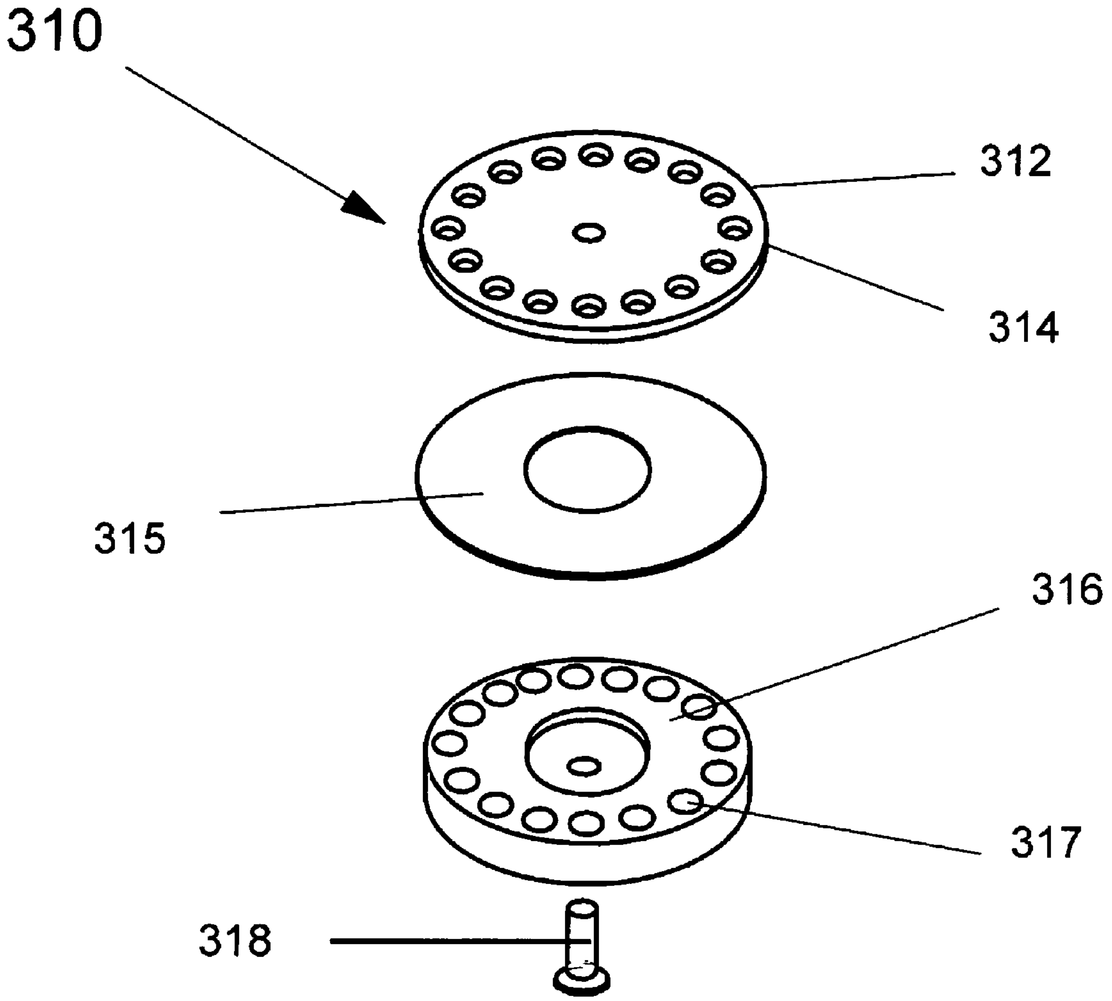
FIG. 6 is a disassembled view of the blister pack of FIGS. 5*a* and 5*b;*

FIGS. 5*a*, 5*b* and 6 show another embodiment of a blister pack 310 that is used to hold multi-doses of a powdered medicament. FIG. 6 shows an exploded view of the same blister pack 310. The blister pack 310 includes a top plate (the holding plate) 312 with multiple blister or blister cells 314 extending through the plate in which the medicament is contained, and a bottom plate 316 with the same number of multiple air passage holes 317 as that of 314 extending through plate 316, with a filter material 315 clamped in between the top plate 312 and bottom plate 316. A set screw 318 is used, preferably going through the centre of plates 312 and 316, to fix the two plates together and to align the pockets 314 in the top holding plate 312 with the holes 317 in the bottom plate 316. Powdered medicament is pre-charged into the blisters 314 and then the blister pack is put into an inhaler. By introducing a gas flow through the air passage holes 317, either by inhalation (suction) from the top of the top plate 312 or by apply pressured air to the bottom of the bottom plate 316, the charged powder medicament will be blown out, to form a powder flow for the pulmonary drug delivery. The main benefit of this embodiment over the blister pack 10 shown in FIG. 1 is that the filter media supported by the bottom plate helps to hold the powdered medicament in place. If the bottom plate 316 and the filter media 315 are both removed after the powder charging and before the blister pack 310 is put into the inhaler, blister pack 310 shown in FIGS. 5*a*, 5*b* and 6 reduces to the blister pack 10 shown in FIG. 1. Filter media 315 may be any inert porous material such as filter paper, fine mesh screens, membrane sheet, and porous solid materials such as porous Teflon and porous ceramics, to mention just a few. It has a pore size to allow gas to flow through but blocks the medicament powder.

After dispensing powder into the blister cells 314, the charged blister pack 310 may be covered on one or both sides with protection layers such as aluminum foils or other protective films to prevent moisture from getting into the blister cells. The film on the top side also helps to hold the powder in the blister cells in place. Before putting the blister pack into the inhaler, the protective films are removed.

The blister cells 314 in the holding plate 312 are normally identical in size and have a fixed or pre-selected volume to store a pre-selected amount of powder therein. By changing the holding plates 312 with different pocket diameters and plate thickness, blister packs 310 of different volumes can be obtained. Any number of blisters 314 can be arranged in any fashion in the plate 312, but for easy use in the inhalers it is beneficial that blister cells 314 are arranged along certain circles on the disk. The bottom plate 316 is provided with air passage holes 317 designed to align with each of the blister cells 314 in plate 312. In the illustrated blister pack of FIGS. 5*a* and 6, both top and bottom plates 312 and 316 are circular and the blisters 314 and holes 317 are arranged on the circumference of a circle in each plate of the same diameter. However, more blister cells 314 and holes 17 may be arranged on multiple circles on each plate.

The blister cells 314 in plate 312 may be made of any shape, although a vertical cylindrical shape is preferred since it is the easiest to produce and to align with the powder outlet and air inlet channels. For example, vertically tapered holes with increasing diameter towards the top surface of plate 312 would be beneficial for the easy charging and blowing-off of the powder, but vertically tapered holes with decreasing diameter towards the top surface of plate 312 would be beneficial for holding the powder in position. The air passage holes 317 in the bottom plate 316 are preferably larger in diameter than the diameter of blister cells 314, to ensure the complete blow-off of powdered medicament in the blister cells 314 by the gas flow through the bottom holes.

As discussed above, in operation, the ratchet wheel 28 (FIG. 2 or 3) is used to rotate the blister pack 310 and to align and hold in place each blister cell 314 aligned with the passageway 32 (as well as passageway 36) through which the powder is to be dispensed. Holding plate 312, filter 315 and bottom plate 316 are locked together and move together about the axis of rotation defined by screw 318.

Figure 7:
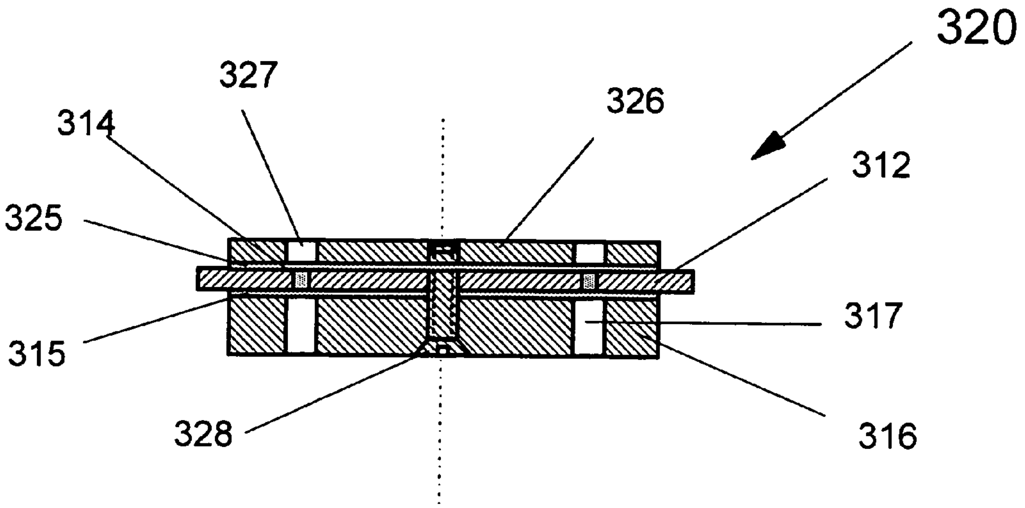
FIG. 7 is a cross sectional view of another embodiment of a blister pack.
Figure 8:
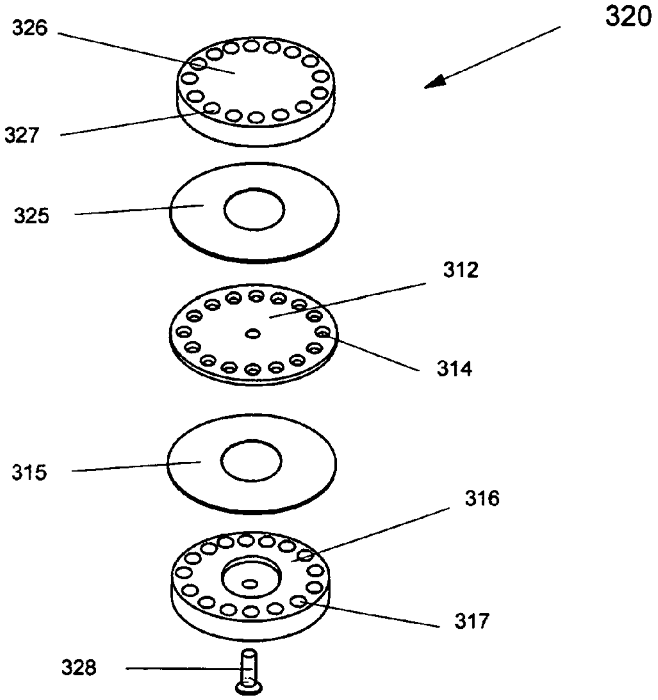
FIG. 8 is a disassembled view of the blister pack of FIG. 7.

Another embodiment of the blister pack is shown generally at 320 in FIG. 7 and with its exploded view shown in FIG. 8. In some cases, the packed powder may not be able to hold together tightly enough so that some particles may easily fall out of the blisters cells. In some other cases, the medicament particles become too sticky that some will stick onto the protective films when peeled before loading into the blisters. Both cases would lead to loss of particles, affecting the accuracy of pulmonary delivery. The embodiment 320 shown in FIG. 7 is useful in preventing the above problems. The blister pack 320 shown in FIG. 7 has the lower parts (312, 314, 315, 316 and 317) identical to the blister pack 310, but with another top plate 326 on top of the holding plate 312, with the same number of multiple air passage holes 327 as that of 314 extending through plate 326, with a filter material 325 clamped in between the top plate 326 and the holding plate 312. The same blister pack as 310 is first charged with powder medicament and then the top plate and filter media are put on to hold the particles in place. The set screw 328, in this case, is longer than the screw 318 in FIG. 5*a* and can be advanced into the top plate 326 after powder loading, so as to fix all three plates together. The holes 327 in the top plate 326 should preferably be equal to, or larger than, the blister holes 314 in the holding plate 312, for easier and more complete powder dispersing and inhalation.

With such an arrangement, the powdered medicament is securely held inside the blister cells during transportation. If protection from moisture is also required, protective films can be sealed against the upper surface of the top plate 326 and the lower surface of the bottom plate 316. Because the protective films are not in direct contact with the medicament particles, there is no potential loss of medicament particles when the films are peeled off before inhalation and usually before loading into the inhalers.

Figure 9:
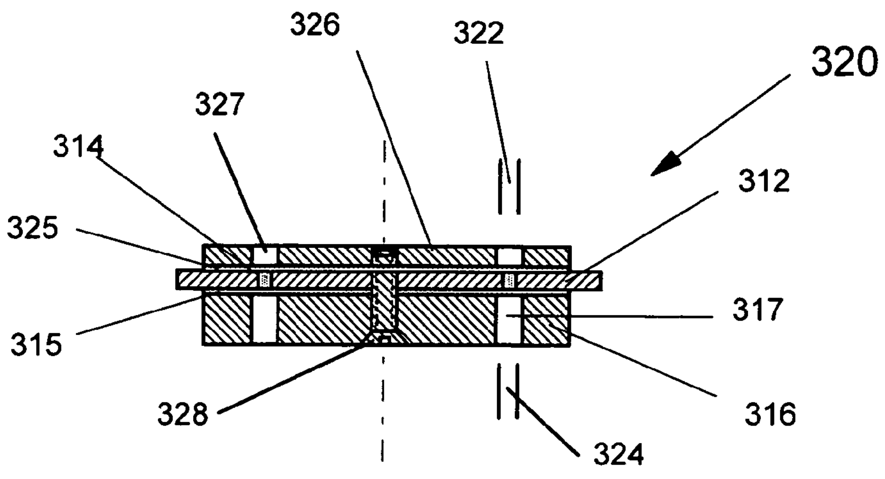
FIG. 9 shows a cross sectional side view of a blister pack and associated piercing mechanism for piercing the filter retaining the powder in the blister pack of FIG. 7.

The above-mentioned blister pack 320 is then loaded into the inhaler, assuming the protective films, if any, have been peeled off. Before inhalation, the top filter media 325 of the blister cell at the position in line with the air inlet passageway 32 and powder outlet passageway 36 must be pierced. This can be realized by a piercing device 322 being pushed into the passageway and onto the filter materials, as shown in FIG. 9. After such piercing operation, the air outlet passage way 36 is open and the blister contents are ready for inhalation.

As discussed above, in operation, the ratchet wheel 28 (FIG. 2 or 3) is used to rotate the blister pack 320 and to align and hold in place each blister cell 314 aligned with the passageway 32 (as well as passageway 36) through which the powder is to be dispensed. Ratchet 28 turns the whole sandwiched assembly, including plate 312/filters 315 and 325/ bottom plate 316 and top plate 326 which move together about the axis of rotation defined by screw 328. In preferred embodiments of the blister discs the various holding plates and top and/or bottom plates are disc-shaped having an axis of rotation about which the ratchet rotates the blister pack.

To further decrease the resistance to the air and powder flow during inhalation, it may be beneficial if the bottom filter media 315 is also pierced open. As shown in FIG. 9, a similar sharp object 324 to that 322 may be used for this purpose. When both the inlet and outlet passageways are open the flow resistance is minimized and the powdered medicament is more easily fluidized and entrained for more efficient pulmonary drug delivery.

Figure 10:
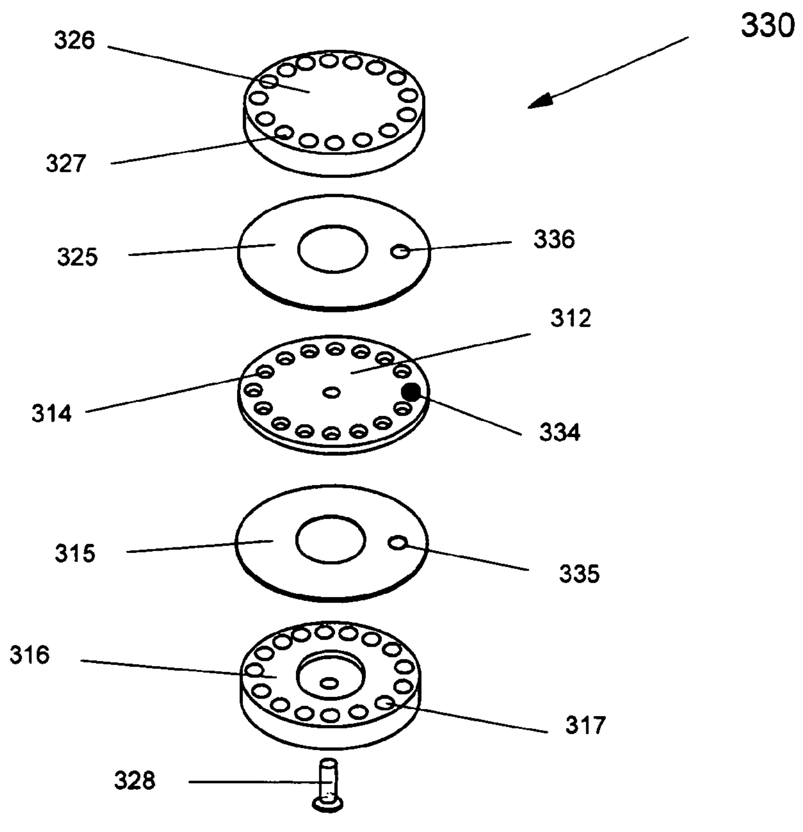
FIG. 10 is a disassembled view of another embodiment of a blister pack that is used to hold multi-doses of a powdered medicament.

An alternative arrangement for reducing the flow resistance but avoiding the use of the piercing objective is shown in FIG. 10. The modified embodiment of blister pack 330 is essentially the same as the blister pack 320 (both preferably being disc-shaped), but the two filter media 315 and 325 each have a hole 335 and 336 respectively in them and one of the blister cells 334 on a modified holding plate 312' is blocked completed (or alternatively not drilled in the first place). As in the case for blister pack 320, the top plate and filter are not put on when loading the powdered medicament into the blister pack. At the loading stage, the open hole 335 in the lower filter media 315 and the blocked hole 334 on the holding plate are aligned together. After loading, the top plate 326 and top filter media 325 are assembled onto the lower portion, with the open hole 336 in the top filter media 325 aligned with the blocked hole 334 on the holding plate 312'. With such arrangement, the blank blister cell with the blocked hole is exposed to the two openings 336 and 335 on the upper and lower filter media 325 and 315 when the blister pack 330 is in storage and transfer, so that there will be no loss of particles.

A preferred apparatus for filling the blister packs for use in the inhalers disclosed herein with the powder medicament is a volumetric metering fluidized bed such as disclosed in U.S. Pat. No. 6,684,917 B2, which is incorporated herein by reference in its entirety, which can be used to precisely dispense a pre-determined amount of pure powdered medicaments (without any excepient) into the powder pockets of the multi-dose blister pack forming part of the dry powder inhaler forming part of the present invention. The device disclosed in U.S. Pat. No. 6,684,917 B2 can deliver a powder plume with approximately 90% or more of the inhalable particles (less than 5 μm in diameter or equivalent aerodynamic diameter) in their primary particle form, that is, with less than 10% particle agglomerates for the small inhalable particles. This ensures the accurate and uniform dispensing of the inhalable particles into the blister cells of the blister pack.

Thus, a preferred method of filling the powder pockets of the blister packs may include producing a fluidized bed in a housing defining an enclosure for containing fine powder medicament where the housing includes a fluid injection mechanism for injecting a fluid into the enclosure for fluidizing the fine powder medicament contained within the housing for forming a dilute phase alone or a dilute phase and a dense phase of fluidized powder medicament. The powder pocket of the blister pack is coupled into flow communication with the enclosure through an outlet passageway for withdrawing pre-selected amounts of the fine powder medicament from housing, and sealing the powder pockets for transporting the pre-filled blister pack.

Figure 11:
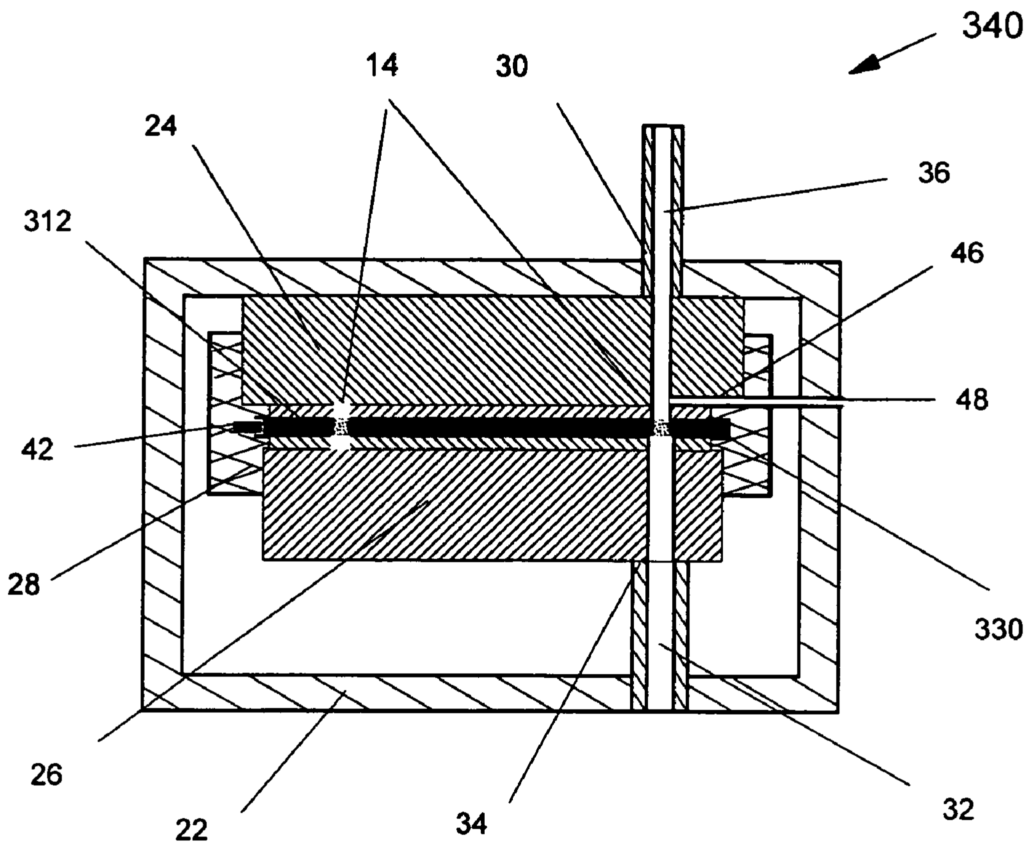
FIG. 11 shows a cross sectional view of another embodiment of an inhaler constructed in accordance with the present invention.

FIG. 11 shows an embodiment of an inhaler at 340 which is similar to inhaler 40, but designed to receive the thicker blister pack 330 shown in FIG. 10. In this case, the top plate 326 in FIG. 10, with the upper filter material 325 will be secured to the top seal block 24 and the bottom plate 316 with the lower filter material 315 will be secured to the bottom seal block 26 in inhaler 340 in FIG. 11 so that the ratchet mechanism is configured to move only the holding plate 312 while the top plate 326 and the bottom plate 316 with filters 325 and 315 attached to each respectively remain in the same fixed position while the holding plate 312' rotates. The holding plate 312 is, however, locked with the ratchet wheel 28. At the initial position, the two openings 335 and 336 on the two filter materials 315 and 325, and the blank blister 334 on the holding plate 312 are aligned together and also aligned with the inlet and outlet passageways 32 and 36. Before inhalation, the ratchet wheel 28 will advance the holding plate 312' to its next position so that the next blister (filled with powdered medicament) will be exposed to the inlet and outlet passageways 32 and 36. Since the passageways are completely open without any filter material in the way, the flow efficiency is greatly increased and the probability for the powdered medicament to be stuck inside the blister is essentially zero. It will be understood that blister pack 330 may be made just using either the bottom plate 316 and filter 315 with the modified holding plate 312' or a combination of both.

It should be noted that other materials can also be used for the blister pack 330. For example, the top and bottom plates 326 and 316 may be replaced with solid plates made from porous materials. This eliminates the need for drilling the very small holes in the plates. In addition, membrane sheets with proper pore size can be formed directly onto one surface of the above-mentioned two plates to act as the filter layers 315 and 325. If the membranes are selected to bond well to the plates, there is no need to use other means to bond the filter layer to the plates. This is particularly useful to ensure membrane layers 315 and 325 stay bound with the top and bottom plates 326 and 316 when the holding plate 312 is rotating with the ratchet wheel 28 being rotated when loaded into the inhaler 340. Another alternative is to use partially porous media to make the top and bottom plates 326 and 316, so that the areas marked as holes 327 and 317 are made porous while all the other areas are solid. This eliminates the needs for filter media 315 and 325.

Figure 12A:
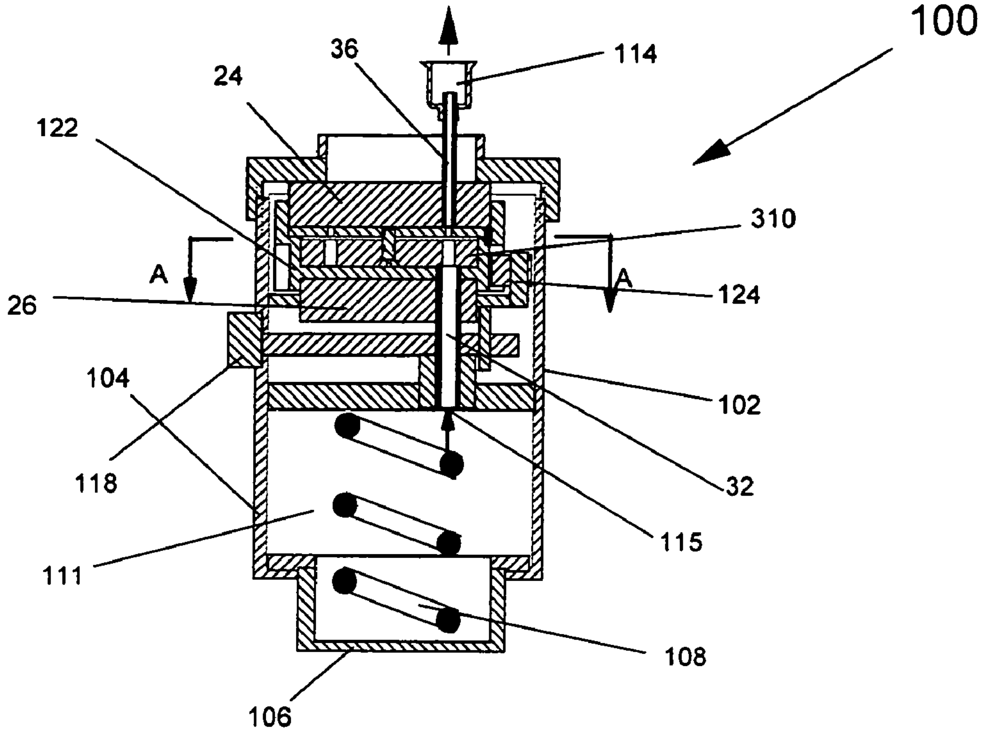
FIG. 12*a* is a cross sectional view of an alternative embodiment of an inhaler.
Figure 12B:
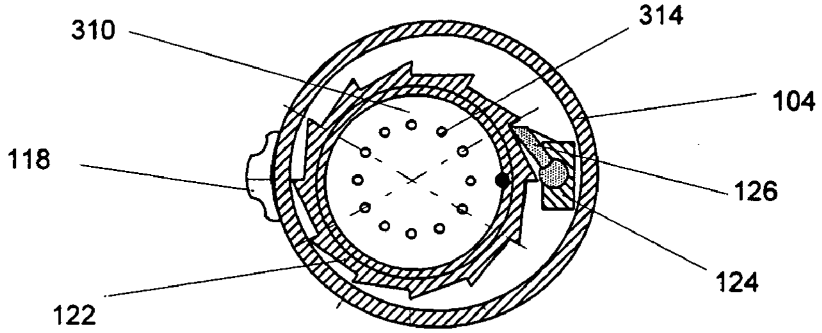
FIG. 12*b* is a cross-sectional top view taken at the A-A plane of the inhaler at 100 in FIG. 12*a;*

Referring now to FIGS. 12*a* and 12*b*, an alternative embodiment of an inhaler shown at 100 includes a housing 102 with two generally cylindrical telescoping sections 104 and 106 with a spring 108 bearing against section 106. Section 106 functions as a push bottom for activating the inhaler to pressurize the air on the interior of the housing for dispensing powder. The top seal block 24 and bottom seal block 26 serve the same function as in the inhalers 20 and 40 in FIGS. 2 and 3 for securing blister pack 310 between them. A mouthpiece 114 is mounted on the powder/air outlet passageway 36.

FIG. 12*b* is a cross-sectional top view at the A-A plane of the inhaler at 100 in FIG. 12*a* and shows the ratchet mechanism for rotating the blister pack 310 which includes a ratchet wheel 122 which is turned by handle 118 with the ratchet wheel 122 engaging a tongue 126 pivotally mounted on a block 124 for locking the blister pack 310 in place thereby controlling the position of the blister cells 314 in blister pack 310. Blister pack rotation handle 118 is connected to the blister pack 310 for rotating the pack into position for dispensing the powder from the different blister cell 314. Air compressed by pushing housing section 106 up into section 104 compresses the air in the chamber 111 defined by housing 104 and 106 which is forced into entrance 115 and up through passageway 32 into the blister cell 314 thereby forcing the powder to be expelled out through outlet passageway 36 and mouthpiece 114.

Figure 12C:
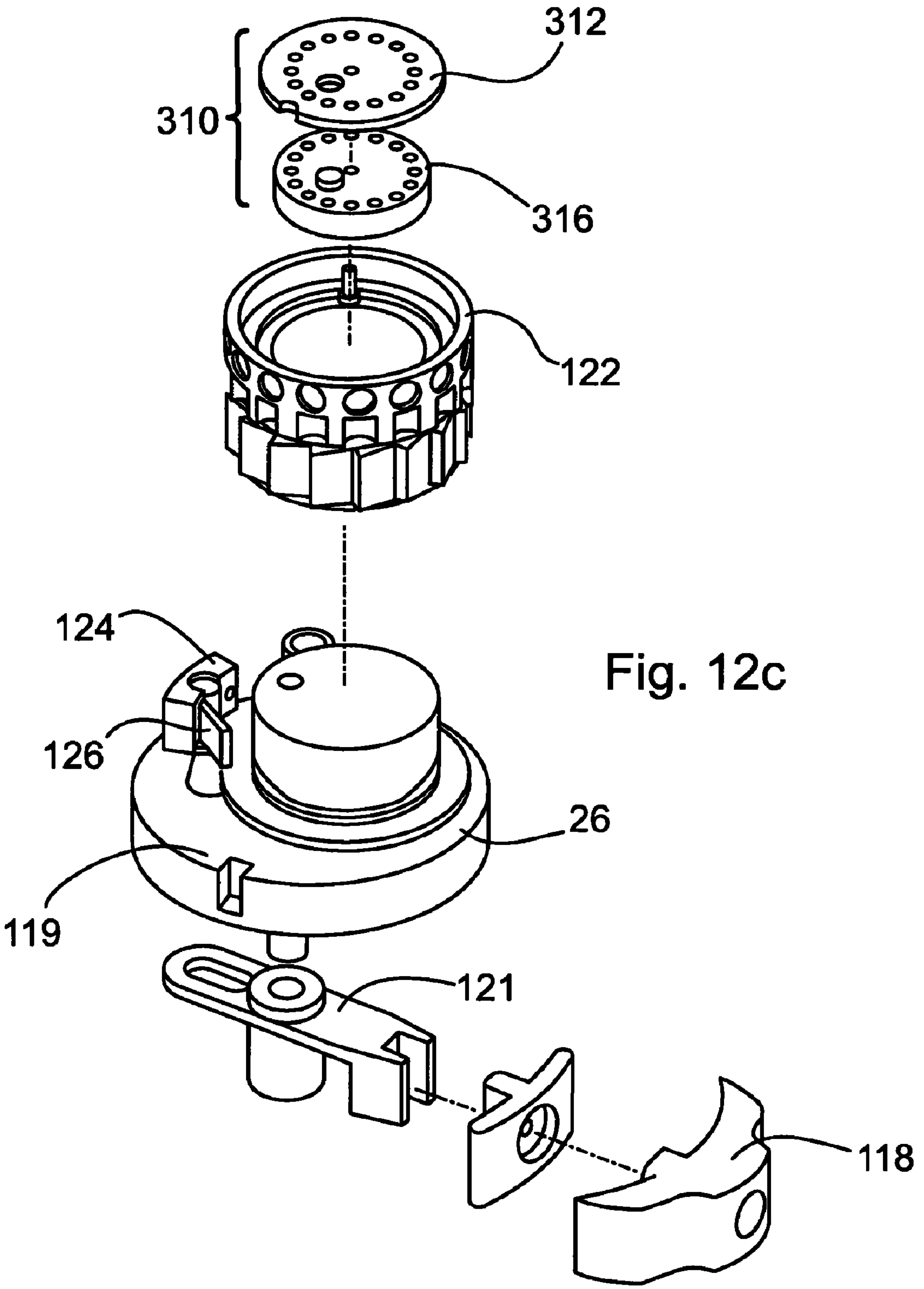
FIG. 12*c* shows an exploded perspective view of the ratchet mechanism for inhalers shown in FIGS. 12*a*, and 120 in FIG. 13*a;*
Figure 13A:
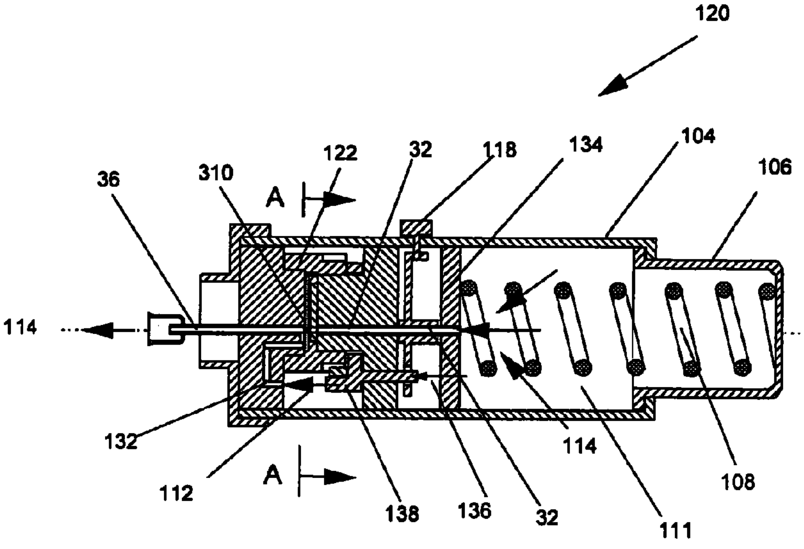
FIG. 13*a* shows a cross sectional view of another embodiment of an inhaler.

FIG. 12*c* shows an exploded perspective view of the ratchet mechanism for inhalers 100 and 120 shown in FIGS. 12*a* and 13*a* but it will be understood that the ratchet mechanisms for the other inhalers are similar. When the handle 118 and lever 121 connected thereto is advanced (counter-clockwise), it turns the ratchet wheel 122 counter-clockwise through a pivotal pin connection 119. The handle 118 and lever 121 then turn clockwise back to its original position. Since the ratchet wheel 122 is engaged with the tongue 126 pivotally mounted on block 124, the ratchet wheel 122 cannot turn back but is locked in the position set by the tongue 126 and the block 124. This locks the blister pack 310 in place thereby controlling the position of the blisters 314. When the dose of powdered medicament in the air flow passageway is inhaled, the handle 118 is advanced again to turn the ratchet wheel 122 which then turns the blister pack 310 to the next position where the next blister cell is aligned for inhalation.

It should be noted that although blister pack 310 is used to illustrate the utility of inhaler 100 in FIG. 12*a*, other blister packs such as 320, 330 or 10 may also be used in combination with inhaler 100. It should also be noted that inhaler 100 as shown in FIG. 12 is a so-called active inhaler where compressed air is used to blow the powdered medicament out of the blister cells. However, inhaler 100 can be easily modified into a passive inhaler where the inhalation force of patient is the sole driving force to lift and then carry the medicament into the patient's lung for pulmonary drug deposition. This can be done by removing the outer housing 106 and the spring 108 and then shorten the length of housing 104.

Figure 13B:
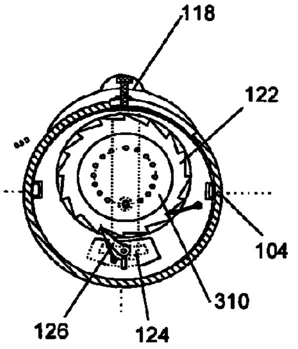
FIG. 13*b* shows a cross-section of the inhaler 120 along the line A-A.
Figure 13C:
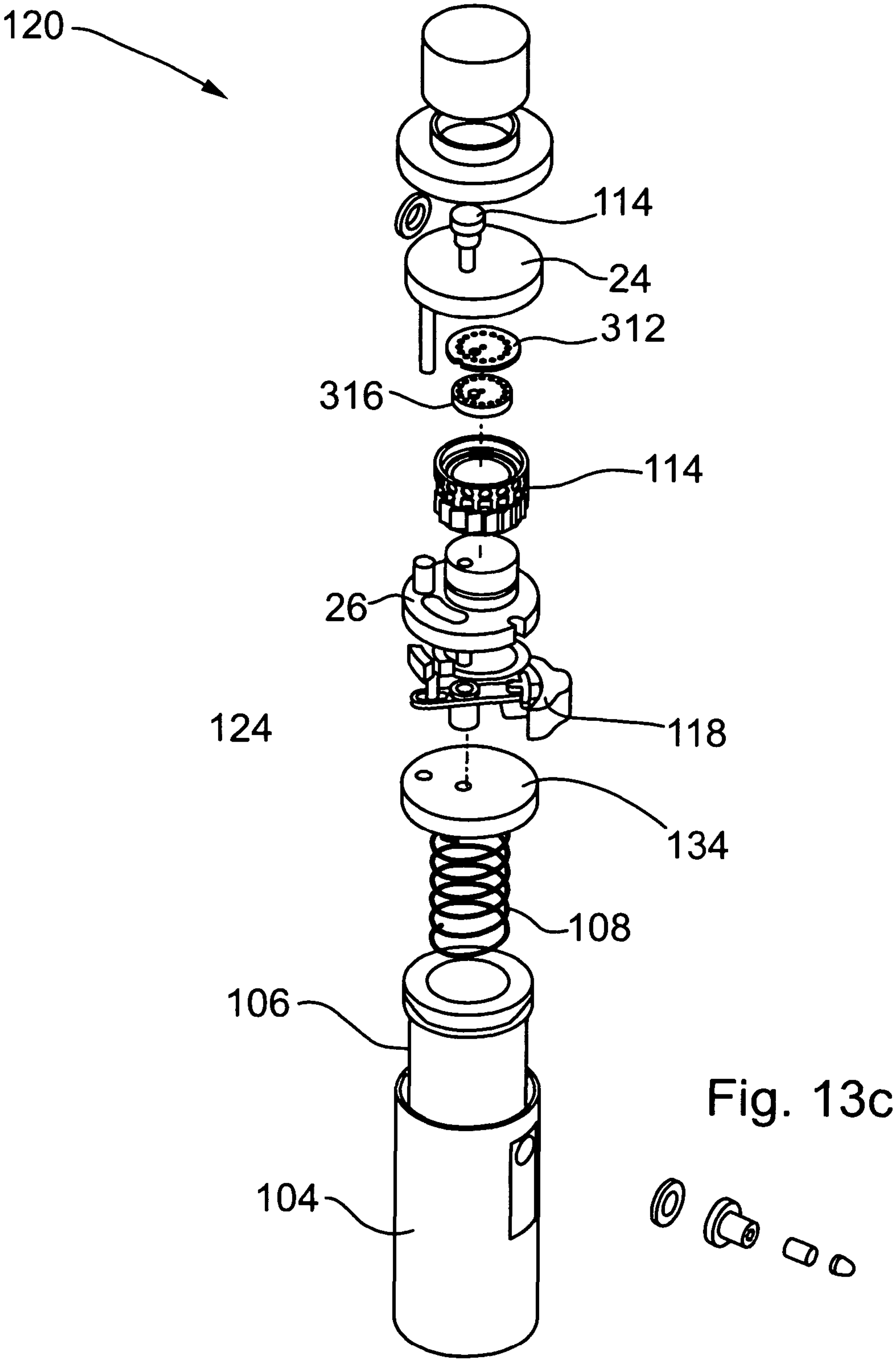
FIG. 13*c* is an exploded perspective view of the inhaler of FIGS. 13*a* and 13*b;*

FIG. 13*a* shows another embodiment of an inhaler shown generally at 120, FIG. 13*b* shows the A-A cross-section of the inhaler 120 and FIG. 13*c* is an exploded perspective view of the inhaler 120. Inhaler 120 is similar in structure to inhaler 100 of FIG. 12*a* but includes an additional secondary air flow passageway 132. This secondary air flow is separated from the major air flow in passageway 32 and is directed into a hidden passageway inside the shaft 138 for the mechanism that turns the ratchet wheel 122. A portion of the compressed air from the chamber 111, other than the portion going through the main air channel 36, passes through the hollow area of the fixed supporting block 134 and then into a passageway located in the shaft 138 (the shaft is not solid, but hollow), as shown by the arrow 136. Air comes out of the inner tube 138 then goes to the secondary air flow passageway 132, as shown by the arrow 112. Eventually, this secondary air flow makes its way through the flow passageway 132, to sweep across the top surface of the blister cell 314 aligned with the outlet passageway 32. This helps to carry the powder out of the pocket into the mouthpiece 114 of the inhaler. The only difference between inhaler 100 and 120 is the presence of this secondary flow passageway 132. FIG. 13*b* shows the mechanism for rotating the blister pack 310 which is essentially the same as the mechanism shown in FIG. 12*b*. Also like inhaler 100, inhaler 120 can also be modified to become a passive inhaler by removing the outer housing 106 and the spring 108 and then shortening the length of housing section 104.

Figure 14A:
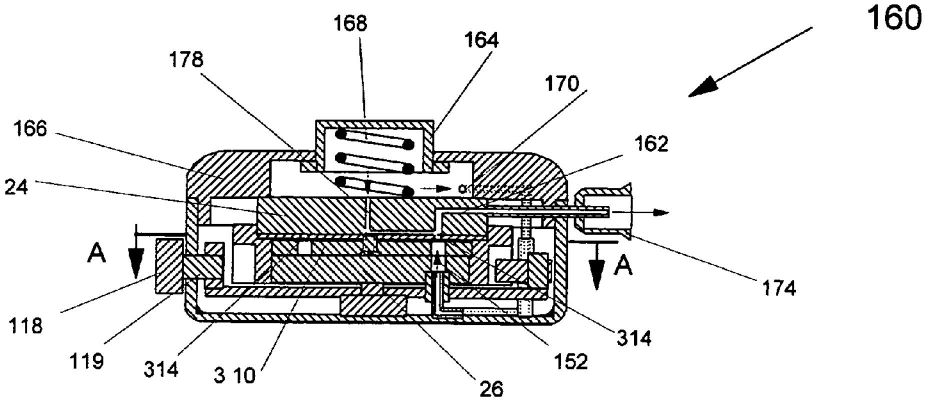
FIG. 14*a* shows a cross sectional view of another embodiment of an inhaler.
Figure 14B:
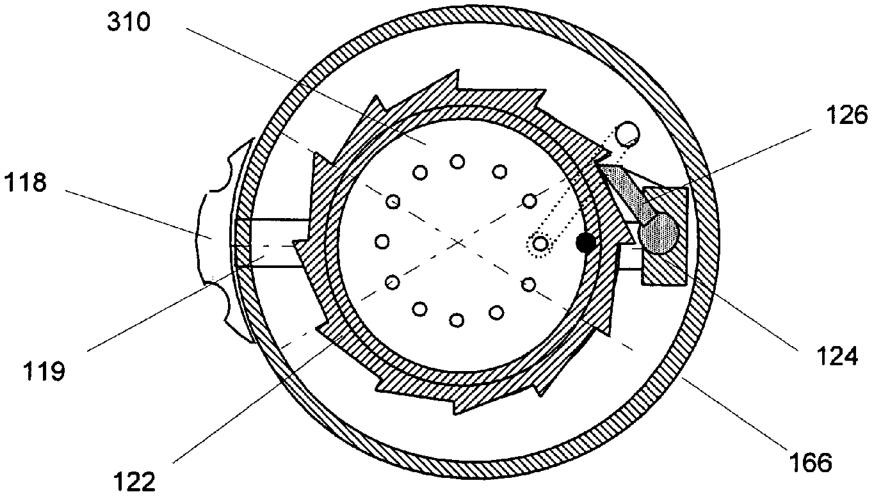
FIG. 14*b* is cross-sectional view along the line A-A of the inhaler in FIG. 14*a;*
Figure 14C:
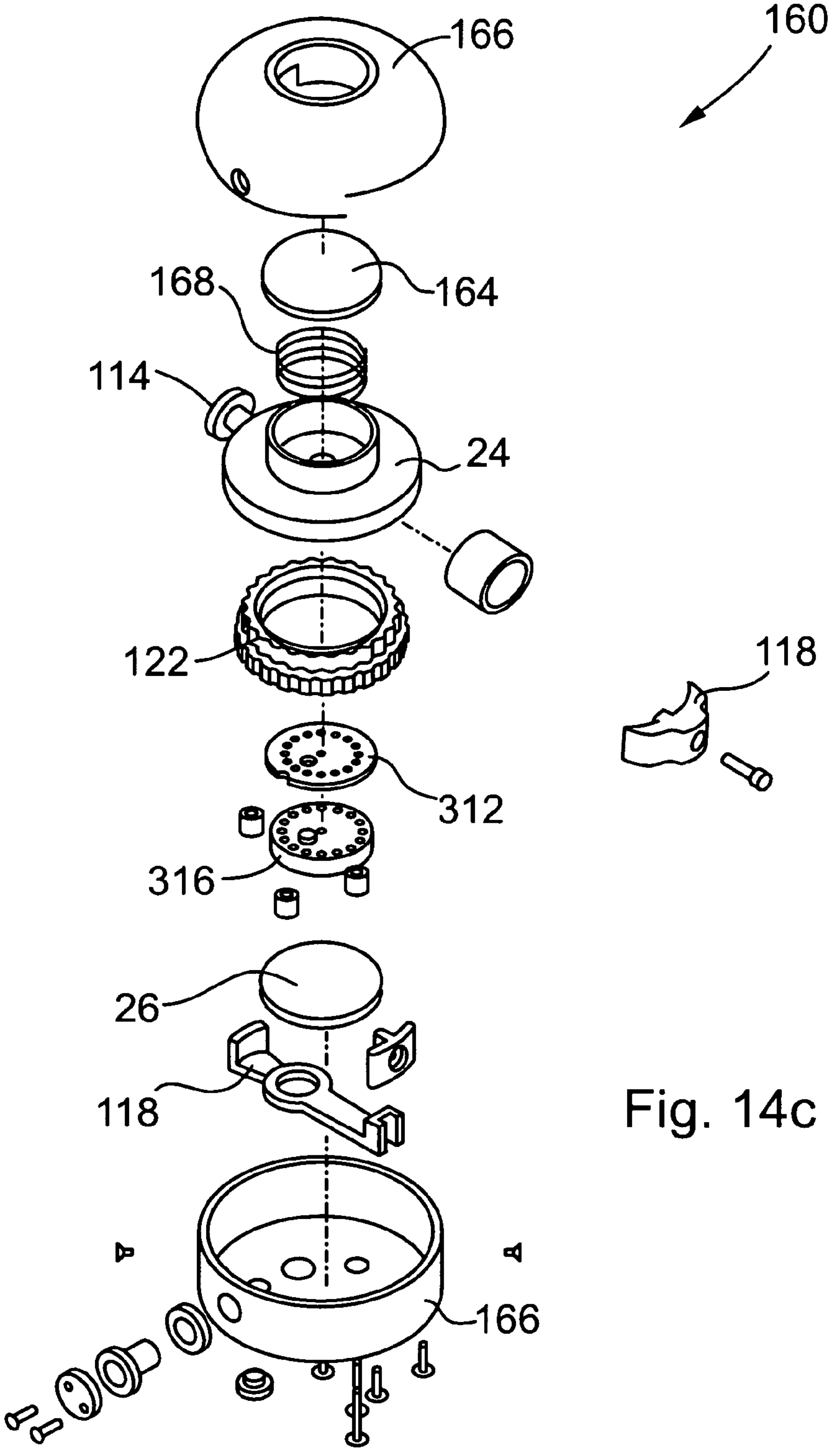
FIG. 14*c* showing an exploded perspective view of the inhaler of FIGS. 14*a* and 14*b;*

FIGS. 14*a* and 14*b* show another alternate embodiment of an inhaler shown generally at 160 with FIG. 14*c* showing an exploded perspective view of the inhaler 160. Inhaler 160 differs from the previous embodiments of the inhaler in that the exit passageway 162 is perpendicular to the direction of the button 164 mounted in telescoping relationship with the housing section 166. Spring 168 returns the button 164 to its rest position. Depressing button 164 acts to compress air within the housing which then enters passageway 170 and exits through exit passageway 162 and mouthpiece 174. There is a secondary air-flow passageway 178 through top seal block 24, which introduces air across the top of the blister cell 314 on blister pack 310 positioned adjacent to the exit passageway 162. Knob 118 and the lever 119 connected thereto is for rotating blister pack 310 to bring the dosages contained in the blisters 314 into alignment with the exit passageway 162 and works the same way as in inhaler 100.

FIG. 14*b* is the A-A cross-sectional view of the inhaler at 160 in FIG. 14*a* and shows the mechanism for rotating the blister pack 310 (similar to FIGS. 12*b* and 13*b*) which includes ratchet wheel 122 which is turned by handle 118 with the ratchet wheel 122 engaging a tongue 126 pivotally mounted on block 124 for locking the blister pack 310 in place thereby controlling the position of the blister cells 314 in blister pack 310. Again, inhaler 160 can also be modified to become a passive inhaler by removing the telescoping button 164 and the spring 168 and then leave some openings in place of the button to allow air inflow.

For inhalers 100, 120 and 160, the blister pack 310 may be centered in the housings as shown for inhaler 160 (see FIG. 14*b*). However, for the inhalers 100 and 120, since both have a vertical design, these inhalers have been constructed so that the position of the blister pack 310 is off-centre in the inhaler housing, in order to minimize the required radius while still accommodating the ratchet turning mechanism. For inhaler 160, because it is of a horizontal design, minimizing the radius is less of a concern than minimizing the total vertical height, the latter being achieved by the positioning the exit passageway 162 perpendicular to the direction of the telescoping housing sections 164 and 166.

Figure 15A:
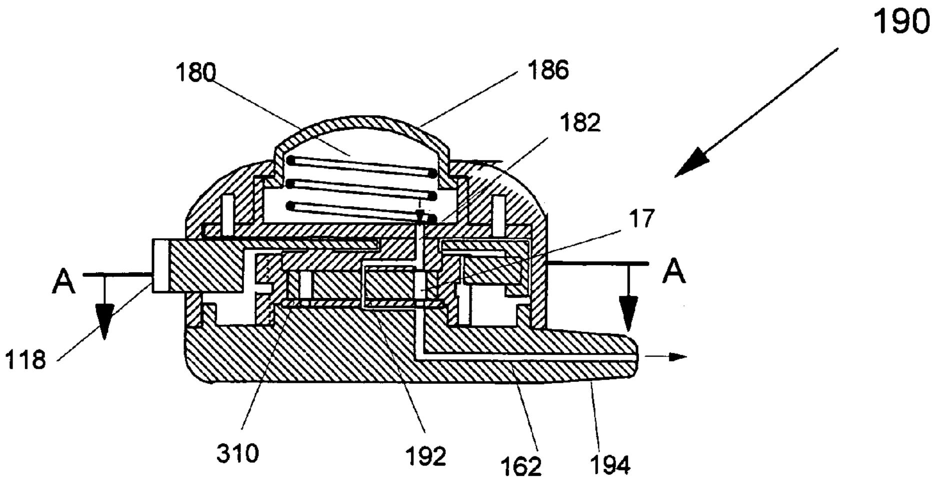
FIG. 15*a* is a cross sectional view of another alternative embodiment of an inhaler.

FIG. 15*a* shows another alternative embodiment of an inhaler shown at 190 which is similar to inhaler 160 of FIG. 14*a*. Inhaler 190 differs from inhaler 160 in that the mouthpiece 194 has been moved to the bottom of the housing so that the main and secondary passageways are shorter with fewer turns. The primary or major air flow passageway 182 directs air to the hole 17 of the blister pack 310, and into passageway 162 which is located in an elongated housing portion 194 forming the mouthpiece which is inserted into the user's mouth, and the secondary air flow passes through a small tube 192 which introduces air across the top of the blister cell 314 on blister pack 310 positioned adjacent to the exit passageway 162.

Figure 15B:
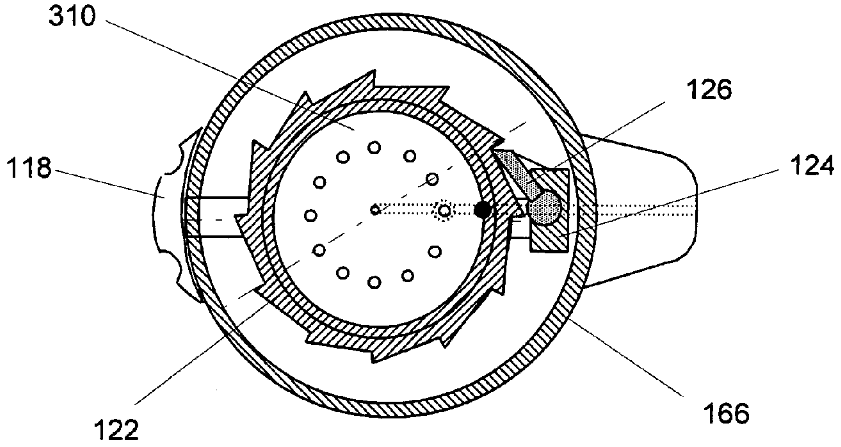
FIG. 15*b* is a cross-sectional view of the inhaler at 190 in FIG. 15*a* taken along the line A-A.
Figure 15C:
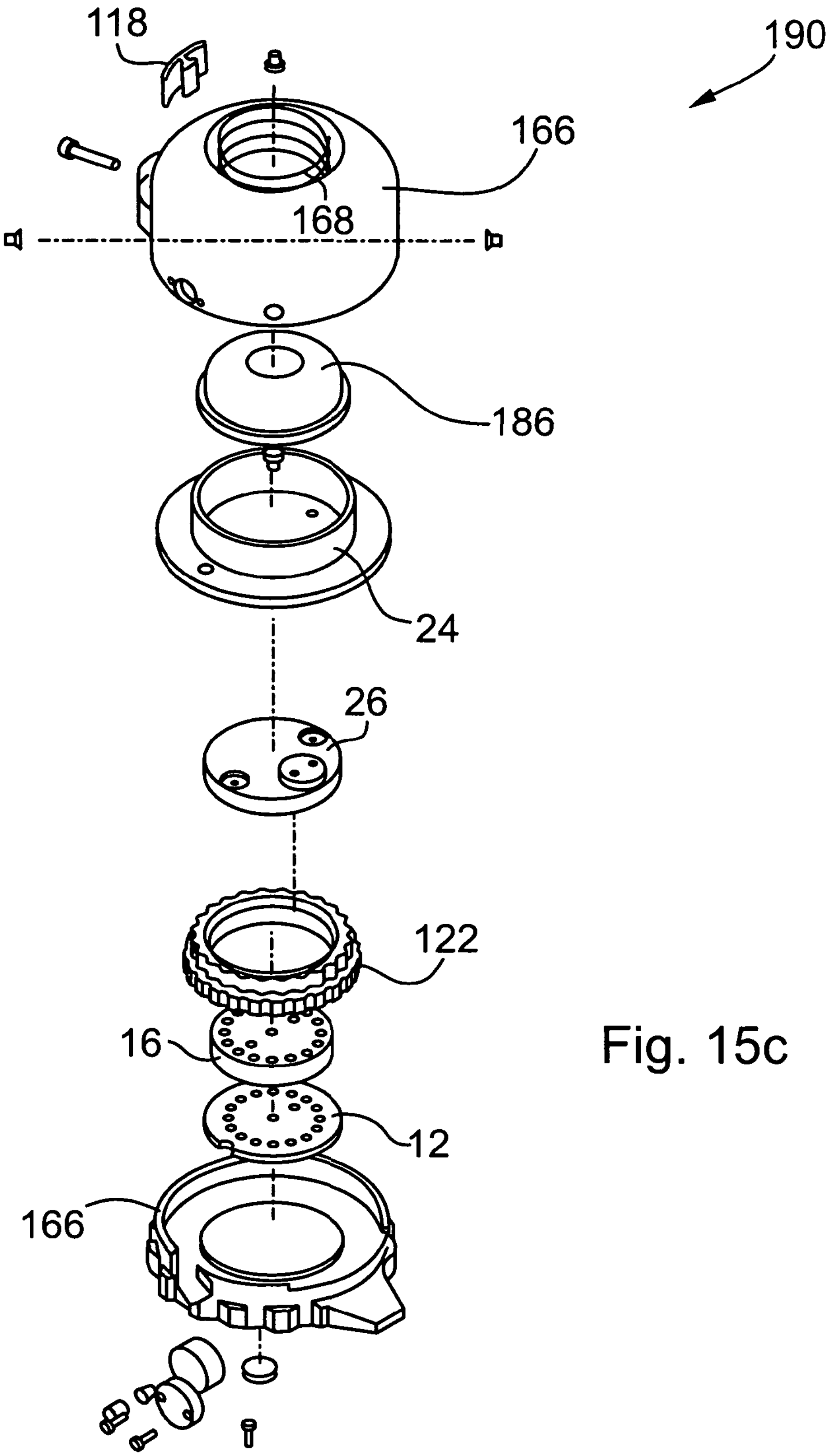
FIG. 15*c* showing an exploded perspective view of the inhaler of FIGS. 15*a* and 15*b;*

FIG. 15*b* shows a view along the line A-A of the inhaler at 190 in FIG. 15*a* and shows the ratchet mechanism for rotating the blister pack 310 (similar to that shown in FIGS. 12*b* and 14*b*). FIG. 15*c* shows an exploded perspective view of inhaler 190. Inhaler 190 can also be modified to become a passive inhaler by removing the telescoping button 186 and the spring 180 and providing one or more air holes in the stationary housing to allow air inflow.

Figure 16:
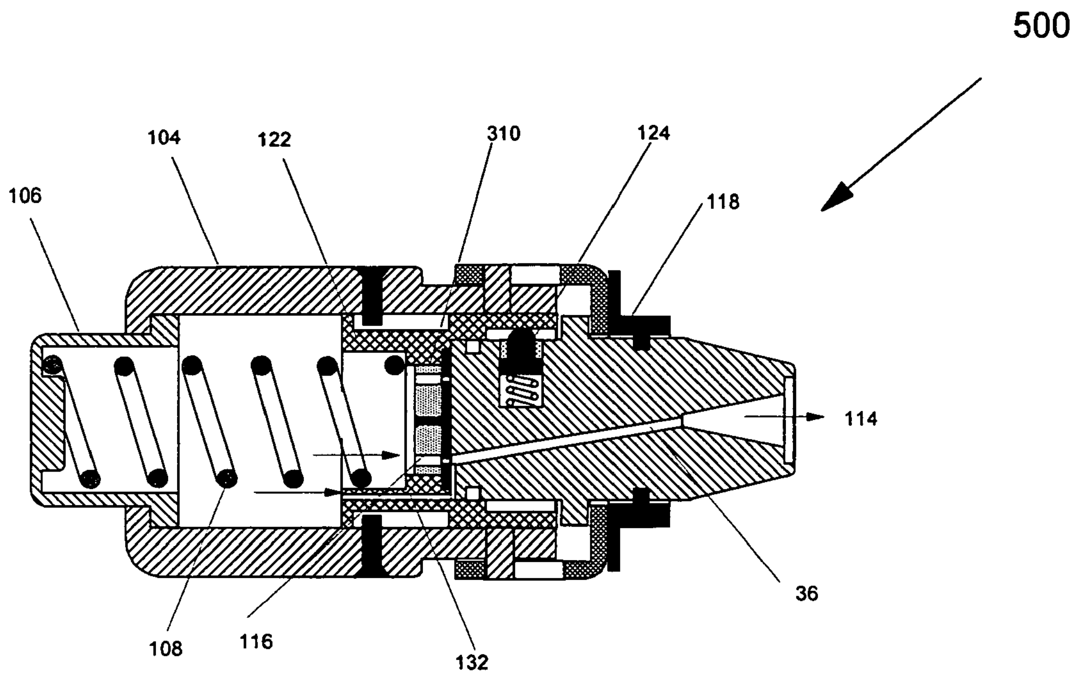
FIG. 16 is a cross sectional view of another embodiment of an inhaler.

FIG. 16 shows another embodiment of an inhaler at 500. Inhaler 500 is similar in structure to inhaler 120 of FIG. 13*a* but has the blister pack 310 located concentrically within the housing 104. All the internal parts in inhaler 500 have the same function as those in inhaler 120, although their relative positions are adjusted and positioned to accommodate the blister pack being concentric within the housing section 104. Inhaler 500 can also be modified to become a passive inhaler by removing the section housing 106 and the spring 108 and then providing air vents so that when a user sucks on the mouthpiece 114 air can be drawn into housing 104 and through hole 116 in the blister pack and secondary passageway 132 so that powder within the blister cell aligned with outlet passageway 36 is drawn into the user's mouth. Optionally the length of housing 104 may be shorted when adapted for the passive mode of operation.

As mentioned above, the inhaler of the present invention is most suitable for the delivery of very small dosages of pure powdered medicaments, giving the very high delivery efficiency. This is particularly useful for the delivery of very expensive medicaments such as peptide and protein drugs, for which the use of excipient will significantly reduce the delivery efficiency and therefore significantly increase the cost. It is also useful for the systemic delivery or localized delivery of any powdered medicament through the lungs.

Thus the present invention provides a method of pulmonary drug delivery of a powder medicament into a patient's respiratory system, which includes filing the powder pockets of a blister pack with a fine powder medicament as discussed above. The fine powder medicament may for example be peptides or fragments thereof, proteins or fragments thereof, antibodies or fragments thereof, antibiotics, vaccines and any combination thereof. The blister pack is loaded into the powder inhaler and the blister pack is moved to bring a powder pocket into flow communication with an outlet flow passageway and a first gas flow inlet passageway, the first gas flow inlet passageway having an inlet in flow communication with a source of gas and an exit located on one side of the powder pocket, said outlet flow passageway having an inlet located on the other side of the powder pocket positioned in flow communication with the outlet flow passageway and an outlet on an exterior of the housing. The powder medicament in the powder pocket which is aligned with the first gas flow inlet and the outlet passageway is fluidized using a first flow of gas from the gas flow inlet passageway which flows into one side of the powder pocket to mobilize, fluidize and deagglomerate the powder medicament such that a mixture of powder medicament and gas flows out through the other side of said powder pocket and into said outlet flow passageway and out of the outlet through a mouthpiece inserted in a user's mouth so that the medicament is expelled out through the mouthpiece and directly into the user's respiratory system. The user can repeat this for as many powder pockets as needed.

This method is very advantageous because the powder medicament does not need to contain any excipient powder particles, but a small amount may be included if desired.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

U.S. Patent Documents

| | | |
|---|---|---|
| 6,546,929 | April 2003 | Burr, et al. |
| 6,325,061 | December 2001 | Dagsland |
| 6,257,732 | July 2001 | Andersson, et al |
| 6,209,538 | April 2001 | Casper, et al. |
| 6,116,239 | September 2000 | Volgyesi |
| 6,089,228 | July 2000 | Smith |
| 6,055,980 | May 2000 | Mecikalski |
| 6,012,454 | January 2000 | Hodson, et al. |
| 6,006,747 | December 1999 | Eisele, et al. |
| 5,975,076 | November 1999 | Yianneskis |
| 5,921,237 | July 1999 | Eisele, et al. |
| 5,785,049 | June 1998 | Smith |
| 5,740,794 | April 1998 | Smith |
| 5,673,685 | October 1997 | Heide, et al |
| 4,627,432 | December 1986 | Newel, et al. |

PUBLICATIONS

1. A. J. Hickey, Inhalation Aerosols: Physical and Biological Basis for Therapy, New York, (1996).
2. Guidance for Industry: Metered Dose Inhaler (MDI) and Dry Powder Inhaler (DPI) Drug Product, U.S. Department of Health and Human Services, 1998.
3. D. Geldart, Types of Gas Fluidization, *Powder Technology*, Vol. 7, 285-297 (1973).

4. I. J. Smith, M. Parry-Billings, The Inhalers of the Future? A Review of Dry Powder devices on the Market Today, *Pulmonary Pharmacology & Therapeutics* 16, 79-95 (2003).
5. C. A. Dunbar, A. J. Hickey and P. Holzner, Dispersion and Characterization of Pharmaceutical Dry Powder Aerosols, *KONA,* 16, 7-45 (1998)
6. M. W. Spallek, J. Geser, H. Reincke, and A. Moser, "Scale-up and production challenges of bringing Respimat Soft-Mist inhaler (SMI) to market", *Respiratory Drug Delivery IX,* 2004.
7. R. Dalby, M. W. Spallek, and T. Voshaar, "A review of development of Respimat SoftMist Inhaler", *int. J. Pharmaceutics*, (2003)

Therefore what is claimed is:

1. A dry powder inhaler for dispensing powder medicament, comprising:

a) a housing and mounting means for mounting a blister pack in an interior of said housing, said blister pack including a holding plate and a plurality of powder pockets substantially filled with a powder comprising a pre-selected amount of powder medicament, each said powder pocket comprising a hole formed between one side of said holding plate and an opposing side of said holding plate, said housing including a first gas flow inlet passageway and an outlet flow passageway, wherein said blister pack includes first porous support means affixed to a bottom surface of said holding plate with the first porous support means having a porosity such that air flows through said first porous support means but the powder medicament does not flow through the first porous support means; and b) positioning means for positioning said blister pack to bring each powder pocket into flow communication with said outlet flow passageway and said first gas flow inlet passageway, said first gas flow inlet passageway having an inlet in flow communication with a source of gas and an exit located in said housing on one side of said holding plate, said outlet flow passageway having an inlet located in said housing on the other side of said holding plate which is positioned in flow communication with said outlet flow passageway and an outlet on an exterior of said housing, wherein when gas from the source of gas is flowed into said first gas flow inlet passageway it flows into one side of said powder pocket and through the powder pocket to mobilize, fluidize and deagglomerate the powder medicament such that a mixture of powder medicament and gas flows out through the other side of said powder pocket and into said outlet flow passageway and out of said outlet.

2. The inhaler according to claim 1 including a second gas flow inlet passageway having an inlet and an exit, said exit being positioned adjacent to the powder pocket which is positioned in flow communication with said outlet flow passageway such that gas in said second gas flow inlet passageway is directed transversely over said other side of said powder pocket to assist fluidization and entrainment of the medicament powder.

3. The inhaler according to claim 2 wherein said positioning means for positioning said blister pack includes a ratchet wheel mounted on an exterior of the housing and connected to the holding plate and wherein the ratchet wheel is rotated in steps to align in turn each of the powder pockets in the holding plate with the first gas flow inlet passageway and the outlet flow passageway.

4. The inhaler according to claim 2 wherein said housing includes first and second housing sections, said first housing section being movable in telescoping relationship to said second housing section with the first and second housing sections forming an airtight seal, including biasing means for biasing said second housing section with respect to said first housing section, wherein said blister pack is mounted in said first housing section, said inlet to said gas flow inlet passageway protruding into an enclosure defined by said second housing section, and wherein when the first and second housing sections are squeezed together, air in an interior of said housing is pressurized thereby producing a compressed air flow through said first and second gas flow passageways, and wherein said biasing means urges the first and second housing sections back apart.

5. The inhaler according to claim 4 wherein said biasing means is a spring bearing against a portion of each housing section.

6. The inhaler according to claim 4 wherein said housing includes a mouth piece protruding therefrom enclosing said outlet flow passageway for a user to insert into their mouth during dispensing of the medicament powder.

7. The inhaler according to claim 4 wherein said first and second gas flow passageways have pre-selected cross-sectional dimensions to give a pre-selected ratio of air flow in the first and second gas flow passageways.

8. The inhaler according to claim 4 wherein said second gas flow passageway includes an adjustable constriction means for adjusting gas flow in said second gas flow passageway for adjusting a ratio of gas flow in the first and second gas flow passageways.

9. The inhaler according to claim 4 wherein said holding plate is disc-shaped having an axis of rotation, and wherein said plurality of holes are arranged in a circle in the holding plate.

10. The inhaler according to claim 9 wherein said positioning means for positioning said blister pack includes a ratchet wheel mounted on an exterior wall of said housing and connected to said disc-shaped holding plate mounted in the interior of said housing for rotating said blister pack about said axis of rotation to move each powder pocket into flow communication with first gas flow inlet passageway and the outlet flow passageway.

11. The inhaler according to claim 4 wherein said first and second housing sections movable in telescoping relationship are generally cylindrical having a longitudinal axis along which the first and second housing sections telescopingly move, and wherein said outlet flow passageway extends through said first housing section generally along said longitudinal axis, and wherein said outlet of the outlet flow passageway on the exterior of said housing is a mouthpiece shaped to be inserted into a user's mouth which extends away from said first housing section generally along said longitudinal axis.

12. The inhaler according to claim 4 wherein said first and second housing sections movable in telescoping relationship are generally cylindrical having an axis along which the first and second housing sections telescopingly move, and wherein said outlet flow passageway extends through said first housing section in a direction generally transverse to said axis, and wherein said outlet of the outlet flow passageway on the exterior of said housing is a mouthpiece shaped to be inserted into a user's mouth which extends away from said first housing section in the transverse direction.

13. The inhaler according to claim 1 wherein said source of gas is air exterior to said housing, wherein said first gas flow inlet passageway is in flow communication with the exterior of said housing, and wherein said mixture of air and powder medicament is drawn out by negative pressure produced by a user applying suction to said outlet of said outlet flow passageway on the exterior of said housing thereby drawing air into said first gas flow inlet passageway.

14. The inhaler according to claim 1 wherein said source of gas is a container containing pressurized gas located in said housing, including activation means connected to said container for releasing pressurized gas from said container and wherein said mixture of air and powder medicament is drawn out by positive pressure resulting from a user activating said activation means thereby forcing gas into said first gas flow inlet passageway.

15. The inhaler according to claim 1 wherein said positioning means for positioning said blister pack includes a ratchet wheel mounted on an exterior of the housing and connected to the holding plate and wherein the ratchet wheel is rotated in steps to align in turn each of the powder pockets in the holding plate with the first gas flow inlet passageway and the outlet flow passageway.

16. The inhaler according to claim 1 wherein said first porous support means is selected from the group consisting of filter paper, membrane sheet, fine mesh screens, porous solid materials, porous Teflon and porous ceramics.

17. The inhaler according to claim 1 wherein said blister pack includes a bottom plate having a same number of holes extending through the bottom plate as contained in the holding plate, and wherein said holding plate and bottom plate are aligned so that the holes line up in each plate, wherein said first porous support means is sandwiched between the bottom surface of said holding plate and a top surface of said bottom plate.

18. The inhaler according to claim 17 wherein said holding plate, said first porous support means and said bottom plate are locked together so that the positioning means moves the holding plate, the first porous support means and the bottom plate together to align in turn each of the powder pockets in the holding plate with the first gas flow inlet passageway and the outlet flow passageway.

19. The inhaler according to claim 18 wherein said positioning means for positioning said blister pack includes a ratchet wheel mounted on an exterior of the housing and connected to the holding plate and wherein the ratchet wheel is rotated in steps to align in turn each of the powder pockets in the holding plate with the first gas flow inlet passageway and the outlet flow passageway.

20. The inhaler according to claim 17 wherein said blister pack includes a top plate having a same number of holes extending through the top plate as contained in the holding plate and bottom plate, and wherein said holding plate and top plate are aligned so that the holes line up in each plate, including a second porous support means sandwiched between a top surface of said holding plate and a bottom surface of said top plate, with the second porous support means having a porosity such that air flows through said second porous support means but the powder medicament does not flow through the second porous support means.

21. The inhaler according to claim 20 wherein said top plate and said second porous support means are locked together with said holding plate, said bottom plate and said first porous support so that the positioning means moves them together to align in turn each of the powder pockets in the holding plate with the first gas flow inlet passageway and the outlet flow passageway.

22. The inhaler according to claim 21 wherein said positioning means for positioning said blister pack includes a ratchet wheel mounted on an exterior of the housing and connected to the holding plate and wherein the ratchet wheel is rotated in steps to align in turn each of the powder pockets in the holding plate with the first gas flow inlet passageway and the outlet flow passageway.

23. The inhaler according to claim 20 including piercing means located in said housing for piercing said second porous support means above a selected powder pocket prior to dispensing the powder medicament from said selected powder pocket.

24. The inhaler according to claim 23 wherein said piercing means is configured to pierce said first porous support means below said selected powder pocket in addition to said second porous support means above said selected powder pocket prior to dispensing the powder medicament from said selected powder pocket.

25. The inhaler according to claim 1 wherein said blister pack includes protective films applied to opposed sides of said holding plate, and wherein said protective films are removed from said blister pack prior to loading said blister pack into said housing.

26. The inhaler according to claim 1 wherein said blister pack includes a bottom plate having a plurality of holes extending through the bottom plate including an additional hole than the number of holes contained in the holding plate, and wherein said holding plate and bottom plate are aligned so that the holes line up in each plate except for said an additional hole in the bottom plate, wherein said first porous support means is sandwiched between the bottom surface of said holding plate and a top surface of said bottom plate, and the first porous support means having a hole extending therethrough and the first porous support means being aligned with the holding plate and the bottom plate such that the hole in the first porous support means is not aligned with any holes in the holding plate but is aligned with said an additional hole in the bottom plate when the blister pack is assembled prior to being inserted into said housing, and wherein when said blister pack is inserted into said housing said hole in said first porous support means is aligned with said outlet flow passageway and said first gas flow inlet passageway, and wherein said bottom plate and said first porous support means is secured in said housing so that they do not move, and wherein said holding plate is engaged by said positioning means to align in turn each of the powder pockets in the holding plate with the first gas flow inlet passageway and the outlet flow passageway.

27. The inhaler according to claim 26 wherein said blister pack includes a top plate having a plurality of holes extending through the top plate with one more additional hole than contained in the holding plate, and wherein said holding plate and top plate are aligned so that the holes line up in each plate except for the one more hole in the top plate, including a second porous support means sandwiched between a top surface of said holding plate and a bottom surface of said top plate, with the second porous support means having a porosity such that air flows through said second porous support means but the powder medicament does not flow through the second porous support means, and the second porous support means having a hole extending therethrough and the second porous support means being aligned with the holding plate and the top plate such that the hole in the second porous support means is not aligned with any holes in the holding plate but is aligned with the hole in the first porous means and the one more additional hole in the top and bottom plates when the blister pack is assembled prior to being inserted into said housing, and wherein when said blister pack is inserted into said housing said hole in said second porous support means is aligned with said outlet flow passageway and said first gas flow inlet passageway, and wherein said top plate and second porous support is secured in said housing so that they do not move, and wherein said holding plate is engaged by said positioning means to align in turn each of the powder pockets in the holding plate with the first gas flow inlet passageway and the outlet flow passageway.

28. The inhaler according to claim 27 wherein said positioning means for positioning said blister pack includes a ratchet wheel mounted on an exterior of the housing and connected to the holding plate and wherein the ratchet wheel is rotated in steps to align in turn each of the powder pockets in the holding plate with the first gas flow inlet passageway and the outlet flow passageway.

29. The inhaler according to claim 1 wherein said housing includes first and second housing sections, said first housing section being movable in telescoping relationship to said second housing section with the first and second housing sections forming an airtight seal, including biasing means for biasing said second housing section with respect to said first housing section, said blister pack being mounted in said first housing section, said inlet to said first gas flow inlet passageway protruding into an enclosure defined by said second housing section, and wherein when the first and second housing sections are squeezed together, air in an interior of said housing is pressurized thereby producing a compressed air flow through said first gas flow inlet passageway.

30. The inhaler according to claim 29 wherein said biasing means is a spring bearing against a portion of each housing section.

31. The inhaler according to claim 29 wherein said housing includes a mouth piece protruding therefrom enclosing said outlet flow passageway for a user to insert into their mouth during dispensing of the medicament powder.

32. The inhaler according to claim 29 wherein said holding plate is disc-shaped having an axis of rotation, and wherein said plurality of holes are arranged in a circle on the holding plate.

33. The inhaler according to claim 32 wherein said positioning means for positioning said blister pack includes a ratchet wheel mounted on an exterior wall of said housing and connected to said disc-shaped holding plate mounted in the interior of said housing for rotating said blister pack about said axis of rotation to move each powder pocket into flow communication with first gas flow inlet passageway and the outlet flow passageway.

34. The inhaler according to claim 1 wherein said holding plate is disc-shaped having an axis of rotation, and wherein said plurality of holes are arranged in two concentric circles, a first circle having a first circumference and a second circle having a second circumference, and wherein said first gas flow inlet passageway includes a branched exit, wherein a first exit of said branched exit is located in said housing such that powder pockets in said first circle are located above the first exit as the holding plate is rotated about said axis of rotation, and wherein a second exit of said branched exit is located in said housing such that powder pockets in said second circle are located above the second exit as the holding plate is rotated about said axis of rotation, and wherein said outlet flow passageway has a branched inlet wherein a first inlet of said branched inlet is located in said housing such that powder pockets in said first circle are located below the first inlet as the holding plate is rotated about said axis of rotation, and wherein a second inlet of said branched inlet is located in said housing such that powder pockets in said second circle are located below the second inlet as the holding plate is rotated about said axis of rotation.

35. The inhaler according to claim 34 wherein said positioning means for positioning said blister pack includes a ratchet wheel mounted on an exterior wall of said housing and connected to said disc-shaped blister pack mounted in the interior of said housing for rotating said blister pack about said axis of rotation to move each powder pockets into flow communication with first gas flow inlet passageway and the outlet flow passageway.

36. The inhaler according to claim 1 wherein said positioning means includes indexing means for indexing a position of each of said plurality of powder pockets relative to said outlet flow passageway.

37. The inhaler according to claim 1 wherein said powder pockets have a volume in a range from about 0.04 to about 0.9 $mm^3$ so that powder medicament stored in each powder pocket is in a range from about 20 μg to about 500 μg.

38. The inhaler according to claim 1 wherein said first gas flow inlet passageway includes an adjustable constriction means for adjusting gas flow in said first gas flow passageway to give a pre-selected air flow rate in the first gas flow passageway.

39. The inhaler according to claim 1 wherein said powder pockets of said blister pack are pre-filled with a fine powder medicament selected from the group consisting of peptides or fragments thereof, proteins or fragments thereof, antibodies or fragments thereof, antibiotics, vaccines and any combination thereof.

40. The inhaler according to claim 1 wherein said outlet of said outlet flow passageway located on the exterior of said housing is a mouthpiece shaped to be inserted into a user's mouth.

41. A method of dispensing a powder medicament contained in a plurality of powder pockets in a blister pack mounted in an inhaler, the method comprising the steps of:

a) moving the blister pack to bring a powder pocket into flow communication with an outlet flow passageway and a first gas flow inlet passageway in the inhaler, the blister pack including a holding plate and the plurality of powder pockets substantially filled with a powder comprising a pre-selected amount of powder medicament, each said powder pocket comprising a hole formed between one side of said holding plate and an opposing side of said holding plate, the first gas flow inlet passageway having an inlet in flow communication with a source of gas and an exit located on one side of the powder pocket, said outlet flow passageway having an inlet located on the other side of the powder pocket positioned in flow communication with the outlet flow passageway and an outlet on an exterior of said housing, wherein said blister pack includes first porous support means affixed to a bottom surface of said holding plate with the first porous support means having a porosity such that air flows through said first porous support means but the powder medicament does not flow through the first porous support means;

b) fluidizing the powder medicament contained in the powder pocket which is aligned with the first gas flow inlet passageway and the outlet passageway using a first flow of gas from the gas flow inlet passageway which flows into one side of the powder pocket and through the powder pocket to mobilize, fluidize and deagglomerate the powder medicament such that a mixture of powder medicament and gas flows out through the other side of said powder pocket and into said outlet flow passageway and out of said outlet;

c) withdrawing said fluidized powder out of said inhaler through said outlet passageway; and d) repeating steps a), b) and c) as many times as needed to dispense a needed amount of the powder medicament.

42. The method according to claim 41 including using a second flow of gas flowed through a second gas flow inlet passageway which directs the second flow of gas laterally across a top of said powder pocket to provide an additional shear fluidization to entrain the fluidized powder in the gas.

43. The method according to claim 42 including adjusting a flow of gas in the first and second gas flow inlet passageways to give a pre-selected ratio of air flow in the first and second gas flow inlet passageways.

44. The method according to claim 42 wherein said first flow of gas is air drawn into said inhaler by negative pressure resulting from a user applying suction to said outlet flow passageway thereby drawing air into the first gas flow inlet passageway which directs air into one side of said powder pocket, and wherein the second flow of gas is air drawn, by said negative pressure, into the second gas flow inlet passageway having an exit which terminates at a position adjacent to the powder pocket located on the other side of the powder pocket so that air in the second gas flow inlet passageway sweeps laterally across the top of the powder pocket.

45. The method according to claim 42 wherein said first flow of gas is air directed into said powder pocket by positive pressure resulting from compressed air released from a pressurized gas container mounted in said inhaler thereby forcing air into the gas flow inlet passageway, and wherein said second flow of gas is air released from said pressurized gas container, into the second gas flow inlet passageway having an exit which terminates at a position adjacent to said powder pocket located above said powder receptacle so that gas in said second flow of gas sweeps across a top of said powder receptacle.

46. The method according to claim 42 wherein said inhaler includes a housing having two telescoping sections with an air tight seal formed between the two telescoping sections, and wherein said first flow of gas is air directed into said powder pocket by positive pressure produced by squeezing the two telescoping housing sections together to compress air in an interior of said housing thereby forcing air into the first gas inlet passageway which directs gas into one side of the powder pocket, and wherein said second flow of gas is produced by said squeezing action thereby forcing gas into the second flow passageway having an exit which terminates at a position adjacent to said powder pocket located on the other side of the powder pocket so that the second flow of gas sweeps across a top of the powder pocket.

47. The method according to claim 42 wherein said powder pockets of said blister pack are pre-filled with a fine powder medicament selected from the group consisting of peptides or fragments thereof, proteins or fragments thereof, antibodies or fragments thereof, antibiotics, vaccines and any combination thereof, and does not include excipient powder particles, and wherein during dispensing of the powder medicament from each powder pocket the fine powder medicament is expelled for direct inhalation into the user's respiratory system.

48. The method according to claim 47 wherein said powder pockets of the blister pack are pre-filled with the fine powder medicament by the steps of;

producing a fluidized bed in a housing defining an enclosure for containing fine powder medicament, said housing including a fluid injection means for injecting a fluid into said enclosure for fluidizing the fine powder medicament contained within said housing for forming a dilute phase alone or a dilute phase and a dense phase of fluidized powder in said housing;

coupling each powder pocket of said blister pack into flow communication with said enclosure through an outlet passageway for withdrawing pre-selected amounts of said fine powder medicament from said housing; and sealing said powder pockets for transporting the pre-filled blister pack.

49. The method according to claim 41 including adjusting a flow of gas in the first gas flow inlet passageway to give a pre-selected air flow rate in the first gas flow inlet passageway.

50. The method according to claim 41 wherein said powder pockets have a volume in a range from about 0.04 to about 0.9 $mm^3$ so that powder medicament stored in each powder pocket is in a range from about 20 μg to about 500 μg.

51. The method according to claim 41 wherein said powder medicament stored in said powder pockets does not include excepient powder particles.

52. The method according to claim 41 wherein said first flow of gas is air drawn into said inhaler by negative pressure resulting from a user applying suction to said outlet flow passageway thereby drawing air into the first gas inlet passageway.

53. The method according to claim 41 wherein said first flow of gas is air directed into said powder pocket by positive pressure resulting from compressed air released from a pressurized gas container mounted in said inhaler thereby forcing air into the gas flow inlet passageway.

54. The method according to claim 41 wherein said inhaler includes a housing having two telescoping sections with an air tight seal formed between the two telescoping sections, and wherein said first flow of gas is air directed into said powder pocket by positive pressure produced by squeezing the two telescoping housing sections together thereby compressing air in an interior of said housing.

55. The method according to claim 41 wherein said powder pockets of said blister pack are pre-filled with a fine powder medicament selected from the group consisting of peptides or fragments thereof, proteins or fragments thereof, antibodies or fragments thereof, antibiotics, vaccines and any combination thereof, and does not include excepient powder particles, and wherein during dispensing of the powder medicament from each powder pocket the fine powder medicament is expelled for direct inhalation into the user's respiratory system.

56. A method of pulmonary drug delivery of a powder medicament into a user's respiratory system, comprising the steps of:

a) substantially filing powder pockets of a blister pack with a powder comprising a fine powder medicament selected from the group consisting of peptides or fragments thereof, proteins or fragments thereof, antibodies or fragments thereof, antibiotics, vaccines and any combination thereof, and loading the blister pack into a dry powder inhaler, wherein said blister pack includes first porous support means affixed to a bottom surface of said holding plate with the first porous support means having a porosity such that air flows through said first porous support means but the powder medicament does not flow through the first porous support means;

b) moving the blister pack to bring a powder pocket into flow communication with an outlet flow passageway and a first gas flow inlet passageway in the dry powder inhaler, the first gas flow inlet passageway having an inlet in flow communication with a source of gas and an exit located on one side of the powder pocket, said outlet flow passageway having an inlet located on the other side of the powder pocket positioned in flow communication with the outlet flow passageway and an outlet on an exterior of said housing;

c) fluidizing the powder medicament contained in the powder pocket which is aligned with the first gas flow inlet passageway and the outlet passageway using a first flow of gas from the gas flow inlet passageway which flows into one side of the powder pocket to mobilize, fluidize and deagglomerate the powder medicament such that a mixture of powder medicament and gas flows out through the other side of said powder pocket and into said outlet flow passageway and out of said outlet through a mouthpiece inserted in a user's mouth so that powder medicament is expelled out through the mouthpiece and directly into the user's respiratory system; and d) repeating steps b) and c) as many times as needed to dispense a needed amount of the powder medicament.

57. The method according to claim 56 wherein said powder does not contain excipient powder particles.

58. The method according to claim 56 wherein said powder contains a small amount of excipient powder particles.

59. The method according to claim 56 wherein said powder pockets of the blister pack are pre-filled with the fine powder medicament by the steps of;

producing a fluidized bed in a housing defining an enclosure for containing particulate matter, said housing including a fluid injection means for injecting a fluid into said enclosure for fluidizing the fine powder medicament contained within said housing for forming a dilute phase alone or a dilute phase and a dense phase of fluidized powder in said housing;

coupling each powder pocket of said blister pack to a flow means connected to said housing and in flow communication with said enclosure through an outlet passageway for withdrawing pre-selected amounts of said fine powder medicament from said housing; and sealing said powder pockets for transporting the pre-filled blister pack.

60. A dry powder inhaler for dispensing powder medicament, comprising:

a) a housing and mounting means for mounting a blister pack in an interior of said housing, said blister pack including a holding plate and a plurality of powder pockets containing a pre-selected amount of powder medicament, each said powder pocket comprising a hole formed between one side of said holding plate and an opposing side of said holding plate, said housing including a first gas flow inlet passageway and an outlet flow passageway, wherein said blister pack includes first porous support means affixed to a bottom surface of said holding plate with the first porous support means having a porosity such that air flows through said first porous support means but the powder medicament does not flow through the first porous support means; and b) positioning means for positioning said blister pack to bring each powder pocket into flow communication with said outlet flow passageway and said first gas flow inlet passageway, said first gas flow inlet passageway having an inlet in flow communication with a source of gas and an exit located in said housing on one side of said holding plate, said outlet flow passageway having an inlet located in said housing on the other side of said holding plate which is positioned in flow communication with said outlet flow passageway and an outlet on an exterior of said housing; and c) a second gas flow inlet passageway having an inlet and an exit, said exit being positioned adjacent to the powder pocket which is positioned in flow communication with said outlet flow passageway;

wherein when gas from the source of gas is flowed into said first gas flow inlet passageway it flows into one side of said powder pocket and through the powder pocket to mobilize, fluidize and deagglomerate the powder medicament such that a mixture of powder medicament and gas flows out through the other side of said powder pocket and into said outlet flow passageway and out of said outlet, and wherein gas in said second gas flow inlet passageway is directed transversely over said other side of said powder pocket to further assist fluidization and entrainment of the medicament powder.

* * * * *